(12) United States Patent
Moraitis

(10) Patent No.: US 11,045,482 B2
(45) Date of Patent: Jun. 29, 2021

(54) USE OF GLUCOCORTICOID RECEPTOR MODULATORS IN THE TREATMENT OF CATECHOLAMINE-SECRETING TUMORS

(71) Applicant: Corcept Therapeutics, Inc., Menlo Park, CA (US)

(72) Inventor: Andreas Moraitis, Menlo Park, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 41 days.

(21) Appl. No.: 15/915,284

(22) Filed: Mar. 8, 2018

(65) Prior Publication Data

US 2018/0256604 A1    Sep. 13, 2018

Related U.S. Application Data

(60) Provisional application No. 62/469,296, filed on Mar. 9, 2017.

(51) Int. Cl.
| | |
|---|---|
| *A61P 5/46* | (2006.01) |
| *A61K 31/575* | (2006.01) |
| *A61P 35/00* | (2006.01) |
| *A61K 31/435* | (2006.01) |
| *A61K 31/517* | (2006.01) |
| *A61K 31/4353* | (2006.01) |
| *A61P 3/00* | (2006.01) |

(52) U.S. Cl.
CPC .......... *A61K 31/575* (2013.01); *A61K 31/435* (2013.01); *A61K 31/4353* (2013.01); *A61K 31/517* (2013.01); *A61P 5/46* (2018.01); *A61P 35/00* (2018.01); *A61P 3/00* (2018.01)

(58) Field of Classification Search
CPC .......... A61K 31/575; A61P 5/46; A61P 35/00
See application file for complete search history.

(56) References Cited

U.S. PATENT DOCUMENTS

| | | | |
|---|---|---|---|
| 6,139,845 A | 10/2000 | Donovan | |
| 6,358,941 B1 | 3/2002 | Snorrason et al. | |
| 6,818,739 B2 | 11/2004 | Sheridan et al. | |
| 7,189,856 B2 | 3/2007 | Shapiro et al. | |
| 7,928,237 B2 | 4/2011 | Clark et al. | |
| 8,461,172 B2 | 6/2013 | Clark et al. | |
| 8,685,973 B2 | 4/2014 | Clark et al. | |
| 8,859,774 B2 | 10/2014 | Hunt et al. | |
| 8,946,154 B2 | 2/2015 | Parente Duena et al. | |
| 2002/0169152 A1 | 11/2002 | Belanoff | |
| 2006/0089299 A1 | 4/2006 | Hsiang et al. | |
| 2010/0178663 A1* | 7/2010 | Graham ........... | G01N 33/57488 435/29 |
| 2015/0038414 A1* | 2/2015 | Lambert ............. | A61K 9/0019 514/11.1 |
| 2015/0148341 A1 | 5/2015 | Hunt et al. | |
| 2016/0310507 A1* | 10/2016 | Belanoff ............. | A61K 31/567 |

FOREIGN PATENT DOCUMENTS

| | | |
|---|---|---|
| WO | 2009050136 A2 | 4/2009 |
| WO | 2013/039916 A1 | 3/2013 |
| WO | WO-2016140867 A1 * | 9/2016 ............. A61K 45/06 |

OTHER PUBLICATIONS

"Chromogranin A: its clinical value as marker of neuroendocrine tumours" by Nobels et al., European Journal of Clinical Investigation (1998) 28, 431-440. (Year: 1998).*
Lacroix et al., "Propranolol Therapy for Ectopic β-Adrenergic Receptors in Adrenal Cushing's Syndrome," N. Engl. J. Med. 1997; 337: 1429-34. (Year: 1997).*
Keiser et al., "Treatment of malignant pheochromocytoma with combination chemotherapy," Hypertension May-Jun. 1985;7(3 Pt 2):I18-24. PMID: 3997232. (Year: 1985).*
Crago et al., "Pheochromocytoma. Treatment with alpha- and beta-adrenergic blocking drugs," JAMA Nov. 27, 1967;202(9):870-74 (Abstract Only). PMID: 6072652. (Year: 1967).*
Nemoto et al., "Sunitinib treatment for refractory malignant pheochromocytoma" (PubMed ABSTRACT), Neuro. Endocrinol. Lett. 2012;33(3):260-264. PMID: 22635080. (Year: 2012).*
Reutter et al., "Importance of detecting rapid changes in blood catechol amine levels in the diagnosis of pheochromocytoma," N. Engl. J. Med. Aug. 15, 1957;257(7):323-5. PMID: 13464934. (Year: 1957).*
Otsuka et al., "An extra-adrenal abdominal pheochromocytoma causing ectopic ACTH syndrome," Am. J. Hypertens. 18(10):1364-68. PMID: 16202863. (Year: 2005).*
Baetge et al., "Complete nucleotide and deduced amino acid sequence of bovine phenylethanolamine N-methyltransferase: Partial amino acid homology with rat tyrosine hydroxylase," Proc Natl Acad Sci USA, Aug. 1986, 83(15): 5454-5458.

(Continued)

*Primary Examiner* — Theodore R. Howell
(74) *Attorney, Agent, or Firm* — Kilpatrick Townsend & Stockton LLP

(57) ABSTRACT

Novel methods of treating tumors, including neuroendocrine tumors (NET), such as a catecholamine-secreting tumor (CST), are disclosed. The methods include treating Cushing's syndrome in a Cushing's syndrome patient having a NET, such as a CST. Tumors may be treated with a glucocorticoid receptor (GR) modulator (GRM), such as a GR antagonist (GRA). The novel treatments may treat Cushing's syndrome, may reduce catecholamine production by the tumor, may reduce catecholamine excess, may ameliorate symptoms of catecholamine excess, and may improve the efficacy of α-adrenergic or β-adrenergic blockade, somatostatin or somatostatin analog treatment or imaging, or Peptide Receptor Radionuclide Therapy, in patients with a CST. The GRM may reduce the activation of a GR, and may bind to a GR with higher affinity than it binds to a progesterone receptor (PR). In embodiments, the drug may only poorly bind to PR, or may not measurably bind to PR.

30 Claims, No Drawings

(56) References Cited

OTHER PUBLICATIONS

Baetge et al., "Transgenic mice express the human phenylethanolamine N-methyltransferase gene in adrenal medulla and retina," Proc Natl Acad Sci USA, May 1988, 85(10):3648-3652.

Batter et al., "The Complete Nucleotide Sequence and Structure of the Gene Encoding Bovine Phenylethanolamine N-Methyltransferase," J Neurosci Res., Mar. 1988, 19(3):367-376.

Ceccatelli et al., "The glucocorticoid receptor in the adrenal gland is localized in the cytoplasm of adrenaline cells," Acta Physiol. Scand. (1989) 137:559-560.

De Bruin et al., Mifepristone Effects on Tumor Somatostatin Receptor Expression in Two Patients with Cushing's Syndrome due to Ectopic Adrenocorticotropin Secretion, J Clin Endocrinol Metab., Feb. 2012, 97(2):455-462.

Finotto et al., "Analysis of mice carrying targeted mutations of the glucocorticoid receptor gene argues against an essential role of glucocorticoid signalling for generating adrenal chromaffin cells," Development, Jul. 1999, 126(13):2935-2944.

Fuxe et al., Mapping of Glucocorticoid Receptor Immunoreactive Neurons in the Rat Tel- and Diencephalon Using a Monoclonal Antibody against Rat Liver Glucocorticoid Receptor, Endocrinology., Nov. 1985, 117(5):1803-1812.

Goodman et al., "Glucocorticoid Induction of Tyrosine Hydroxylase in a Continuous Cell Line of Rat Pheochromocytoma," J. Cell Biol. (1978), 78(1):R1-R7.

Grouzmann et al., Catecholamine Metabolism in Paraganglioma and Pheochromocytoma: Similar Tumors in Different Sites? PLoS One (2015), 10(5):e0125426, pp. 1-18.

Gustafsson et al., "Biochemistry, Molecular Biology, and Physiology of the Glucocorticoid Receptor," Endocr Rev., May 1987, 8(2):185-234.

Isobe et al., "Enhanced Expression of mRNA Coding for the Adrenaline-Synthesizing Enzyme Phenylethanolamine-N-Methyltransferase in Adrenaline-Secreting Pheochromocytomas," J. Urol. (2000) 163:357-362.

Kaneda et al., "Molecular Cloning of cDNA and Chromosomal Assignment of the Gene for Human Phenylethanolamine N-Methyltransferase, the Enzyme for Epinephrine Biosynthesis," J Biol Chem., Jun. 5, 1988, 263(16):7672-7677.

Morita et al., "Organization and complete nucleotide sequence of the gene encoding mouse phenylethanolamine N-methyltransferase," Brain Res Mol Brain Res., May 1992, 13(4):313-319.

Rohrer et al., "Rapid Identification of Subtype-Selective Agonists of the Somatostatin Receptor Through Combinatorial Chemistry," Science (1998), 282(5389):737-740.

Rosas et al., "Pheochromocytoma crisis induced by glucocorticoids: a report of four cases and review of the literature," Eur J Endocrinol. (2008), 158(3):423-429.

Ross et al., "Identification of a Functional Glucocorticoid Response Element in the Phenylethanolamine N-Methyltransferase Promoter Using Fusion Genes Introduced into Chromaffin Cells in Primary Culture," (rat) J Neurosci., Feb. 1990, 10(2):520-530.

Schmid et al., "Molecular Genetic Analysis of Glucocorticoid Signalling in Development," J Steroid Biochem Mol Biol., Jun. 1995, 53(1-6):33-35.

Tai et al., "Glucocorticoid Responsiveness of the Rat Phenylethanolamine N-Methyltransferase Gene," Mol Pharmacol. (2002), 61(6):1385-1392.

Tischler et al., "Glucocorticoids Increase Catecholamine Synthesis and Storage in PC 12 Pheochromocytoma Cell Cultures," J. Neurochem (1983), 40(2):364-370.

Wurtman et al., "Control of Enzymatic Synthesis of Adrenaline in the Adrenal Medulla by Adrenal Cortical," J. Biol. Chem. (May 25, 1966), 241(10):2301-2305.

Ziegler, CG et al., "Anti-Tumor effects of peptide analogs targeting neuropeptide hormone receptors on mouse pheochromocytoma cells", Molecular and Cellular Endocrinology; vol. 371, Issue 2, pp. 189-194; May 22, 2013.

International Search Report and Written Opinion from Application No. PCT/US2018/021592, dated Jun. 15, 2018.

PCT/US2018/021592, "Invitation to Pay Additional Fees and Partial Search Report", dated Apr. 13, 2018, 2 pages.

Sartor et al., "Mifepristone: Treatment of Cushing's Syndrome", Clinical Obstetrics Gynecol, vol. 39, No. 2, Jun. 1996, pp. 506-510.

Application No. EP18763240.1, Extended European Search Report, dated Nov. 12, 2020, 9 pages.

* cited by examiner

USE OF GLUCOCORTICOID RECEPTOR MODULATORS IN THE TREATMENT OF CATECHOLAMINE-SECRETING TUMORS

CROSS-REFERENCE TO RELATED APPLICATIONS

This application claims the benefit of, and priority to, U.S. Provisional Patent Application Ser. No. 62/469,296, filed Mar. 9, 2017, the entire contents of which is hereby incorporated by reference in its entirety.

BACKGROUND

Cushing's syndrome is characterized by excessive cortisol levels. Cushing's syndrome is accompanied by hypercortisolemia, a condition involving a prolonged excess of circulating cortisol. Cushing's syndrome can be classified as exogenous Cushing's syndrome, which is caused by excess use of glucocorticoids drugs, such as prednisone, dexamethasone, and hydrocortisone, and endogenous Cushing's syndrome, which is caused by deregulatory abnormalities in the HPA axis. Patients having Cushing's syndrome usually have easy bruising; abdominal obesity and thin arms and legs; facial plethora; acne; proximal muscle weakness; and/ or red purple stripes across the body.

In endogenous Cushing's, the excess cortisol is typically due either to a tumor producing cortisol, or to a tumor indirectly raising cortisol levels (e.g., by causing increased adrenocorticotropic hormone (ACTH) or causing increased corticotropin-releasing hormone (CRH)). Endogenous Cushing's syndrome consists of the ACTH-independent Cushing's syndrome, characterized by an overproduction of cortisol in the absence of elevation of ACTH secretion; the ACTH-dependent Cushing's syndrome, characterized by excessive ACTH secretion. ACTH-dependent Cushing's syndrome includes roughly 80% of patients having endogenous Cushing's syndrome and consists of two major forms: Cushing Disease and ectopic ACTH syndrome. The former is caused by a pituitary tumor and the latter is caused by a tumor outside the pituitary. Those Cushing's syndrome cases caused by excess ACTH secretion by the pituitary are also termed Cushing's disease.

Pheochromocytoma (PHEO) and paraganglioma (PGL) are tumors arising from chromaffin cells that derive from the embryonic neural crest. The majority of PHEO/PGL cases are known as sporadic tumors while mutations in genes including VHL (von Hippel-Lindau), RET (Multiple Endocrine Neoplasia type 2), NF1 (Neurofibromatosis type 1), SDH (Succinate Dehydrogenase subunits A, B, C and D) and cofactor SDHAF2, MAX (MYC associated factor X), HIF2A (hypoxia-inducible factor 2A), FH (fumarate hydratase) and TMEM127 (transmembrane protein 127) account for approximately 40% of tumors. PGL are more likely to develop metastasis with an incidence rate of approximately 10% of total PHEO/PGL cases. Both types of tumors produce and usually secrete larger amounts of catecholamine (CAT) than the adrenal medulla, due to an up-regulation of tyrosine hydroxylase (TH) and dopamine β-hydroxylase (DBH) the main enzymes responsible for CAT synthesis. In chromaffin cells and pheochromocytes, norepinephrine (NE) and epinephrine (E) are stored in vesicles where they sustain a passive leakage into the cytoplasm before being recaptured in the vesicle pool. The adrenal medulla is by far the most important site of E production in the body since phenyl ethanolamine N-methyltransferase (PNMT), the enzyme that transforms NE into E, is largely restricted to this tissue and absent from sympathetic nerves (that only produce NE).

Glucocorticoids play a major role in the regulation of catecholamine synthesis. Wurtman et al. showed that hypophysectomy in rats was associated with a significant decline in adrenal weight and an even greater fall in PNMT activity.

Grouzmann et al. (PLoS ONE 10(5):e0125426 (2015)) measured the effects of glucocorticoids on TH, DBH and PNMT gene transcription and protein expression in catecholamine-secreting tumors. To assess experimentally the effects of GC on PNMT, TH and DBH gene expression in primary cell culture, cells from 4 PGL and 9 PHEO (6 mixed and 3 NorAd tumors) were plated in culture dishes and incubated with or without dexamethasone for 24 hrs. In PGL cells no significant effect on PNMT mRNA was detected. DBH and TH mRNA were below quantification limit due to low material amount available after surgical resection and lower qPCR efficiency for these two genes compared to PNMT. In PHEO cells dexamethasone induced a 2.8 fold upregulation of TH compared with non-dexamethasone-incubated cells at 24 hrs, no effect was recorded for DBH and PNMT and between mixed vs. noradrenergic PHEO regarding gene transcription for TH, DBH and PNMT after 24 hrs incubation with dexamethasone. To correlate gene with protein expression, TH, DBH and PNMT protein concentration was revealed from dexamethasone incubated and control cells after 24 hrs incubation. Absence of activation was confirmed for DBH and PNMT in steroids incubated cell compared to control cells while TH up-regulation detected for mRNA was not confirmed at the protein level.

Goodman et al. (J. Cell Biol. 78(1):R1-R7 (1978)) in a continuous cell line derived from a rat pheochromocytoma tumor showed a glucocorticoid driven increase in the synthesis of the enzyme tyrosine hydroxylase, the rate-limiting step in the adrenergic pathway.

Glucocorticoids are critical regulators of phenylethanolamine N-methyltransferase (PNMT), the final enzyme in epinephrine biosynthesis, exerting both transcriptional and post-transcriptional influences. In vivo studies in rats have shown that depletion of corticosteroids by hypophysectomy decreases PNMT mRNA and enzyme expression. These changes can be reversed by administration of adrenocorticotropin, which stimulates endogenous glucocorticoid production, or direct corticosteroid replacement by administration of the synthetic glucocorticoid dexamethasone. Changes in PNMT enzyme are a consequence of alterations in both gene transcription and proteolytic degradation. Glucocorticoids increase not only the secretion of catecholamines but also the storage of CAT in the chromaffin cells.

When intact rats are administered either dexamethasone or the glucocorticoid agonist RU28362, PNMT mRNA levels rise markedly. Although it remains unclear whether glucocorticoids are essential for PNMT transcriptional activity, glucocorticoid receptor-deficient mice do not express adrenal medullary PNMT although chromaffin cells are otherwise ostensibly normal (Schmid et al., J Steroid Biochem Mol Biol. 53:33-35 (1995); Finotto et al., Development 126:2935-2944 (1999)). Glucocorticoid-induced transcriptional changes are mediated through glucocorticoid response elements (GREs) in the proximal 5-flanking sequences of the PNMT gene promoter. At least one putative GRE has been identified for every species-specific PNMT gene, including human (Baetge et al., Proc Natl Acad Sci USA. 85(10):3648-3652 (1988); Kaneda et al., J Biol Chem.

263(16):7672-7677 (1988)); cow (Baetge et al., Proc Natl Acad Sci USA 83(15):5454-5458 (1986); Batter et al., J Neurosci Res. 19(3):367-376 (1988)); rat (Ross et al., J Neurosci. 10(2):520-30 (1990)); and mouse (Morita et al., Brain Res Mol Brain Res. 13(4):313-319 (1992)). In the case of the rat PNMT gene, a GRE was identified at −533 bp when the gene was first cloned (Ross et al., 1990). Although this GRE seemed to be functional, its responsiveness to glucocorticoid activation seems both variable and weak.

Tai et al. (Mol Pharmacol. 61(6):1385-1392 (2002)) identified two, overlapping (1 bp) glucocorticoid response elements (GREs) at −759 and −773 bp in the promoter of the rat phenylethanolamine N-methyltransferase (PNMT) gene are primarily responsible for its glucocorticoid sensitivity, rather than the originally identified −533-bp GRE. A dose-dependent increase in PNMT promoter activity was observed in RS1 cells transfected with a wild-type PNMT promoter-luciferase reporter gene construct and treated with dexamethasone (maximum activation at 0.1 μM). The type II glucocorticoid receptor antagonist RU486 (10 μM) fully inhibited dexamethasone (1 μM) activation of the PNMT promoter, consistent with classical glucocorticoid receptors mediating corticosteroid-stimulated transcriptional activity. The glucocorticoid receptor bound to the −759- and −773-bp GREs interacts cooperatively with Egr-1 and/or AP-2 to stimulate PNMT promoter activity in RS1 cells treated with dexamethasone. In contrast, glucocorticoid receptors bound to the −533-bp GRE only seem to participate in synergistic activation of the PNMT promoter through interaction with activator protein 2.

Further proof for the role of cortisol in catecholamine-secreting tumors provided by Isobe et al. (J. Urol. 163:357-362 (2000)). The capacity for cortisol production locally in the pheochromocytoma tissues is further supported by the expression of a glucocorticoid biosynthetic enzyme, 17a-hydroxylase, in the tumors. PNMT expression was found to be associated with 17a-hydroxylase expression in the tumors. The glucocorticoid receptor expression was also correlated with PNMT expression in the tumors.

The medulla and ganglia are both parts of the autonomous nervous system. The distribution of glucocorticoid receptor-like immunoreactivity (GR-LI) in the CNS has been previously described in detail (Fuxe et al. Endocrinology 117(5): 1803-1812 (1985), Gustafsson et al. Endocr Rev. 8(2):185-234 (1987)), but in all brain regions the immunoreactivity was localized to the nucleus of the cell bodies. Ceccatelli et al. (Acta Physiol. Scand. 37:559-560 (1989)) have shown that the presence of GR-LI only in the cytoplasm of chromaffin cells in the adrenal gland that was unexpected. The double staining experiment (GR and PNMT) revealed that the GR-LI was to a large extent confined to PNMT-immunoreactive cell bodies, i.e. the adrenaline cells. This localization is in good agreement with the early work of Wurtman and Axelrod (J. Biol. Chem. 241(10):2301-23015 (1966)) demonstrating the importance of steroids for the PNMT synthesis.

Several isolated cases of pheochromocytoma crisis (PC) have been reported after administration of exogenous glucocorticoids; evidence that these drugs cause adverse events in patients with pheochromocytoma is mainly anecdotal. Rosas et al. (Eur J Endocrinol. 158(3):423-429 (2008)) have reported four cases of pheochromocytoma crisis triggered by exogenous glucocorticoids. During the investigation of incidental adrenal masses, pheochromocytoma should ideally be ruled out before administering glucocorticoids. However, no cases have been reported with 1 mg of dexamethasone when given as a DST in patients with pheochromocytoma; larger doses, as low as 2 mg of dexamethasone, may trigger a PC. A patient with pheochromocytoma presenting as an adrenal incidentaloma may also be at risk if exposed to glucocorticoids given as pre-treatment in case of allergy to contrast media.

Somatostatin receptors type 1 (sst1) and 2 (sst2) are expressed in both paragangliomas and pheochromocytomas. De Bruin et al. (J Clin Endocrinol Metab. 97(2):455-62 (2012)) have shown that hypercortisolemia downregulates the expression of somatostatin receptors type 2 (sst2). Somatostatin analogs which bind to somatostatin receptors are currently on clinical trials in patients with catecholamine-secreting tumors. Although patients with catecholamine-secreting tumors are usually normocortisolemic it is possible that increased cortisol activity at the tumor level could affect the expression of sst2 and as a result could affect the efficacy of somatostatin analogs.

The current treatment for metastatic catecholamine-secreting tumors includes chemotherapy with cyclophosphamide, vincristine and dacarbazine. Other available chemotherapies that are currently in clinical trials include tyrosine kinase inhibitors. Finally, patients with metastatic disease without large lesions might be eligible for MIBG therapy.

Cushing's syndrome patients may have catecholamine-secreting tumors.

Accordingly, there exist needs for therapies and for compositions for treating patients having neuroendocrine tumors, including for treating patients having catecholamine-secreting tumors. In particular, there exist needs for therapies and for compositions for treating Cushing syndrome patients having neuroendocrine tumors, including for treating Cushing syndrome patients having catecholamine-secreting tumors.

SUMMARY

The present application discloses novel methods of treating tumors, including neuroendocrine tumors, such as, for example, catecholamine-secreting tumors. The present application discloses novel methods of treating Cushing syndrome in patients having tumors, including neuroendocrine tumors, such as, for example, catecholamine-secreting tumors. In embodiments, a catecholamine-secreting tumor is contacted with a glucocorticoid receptor modulator; in embodiments, a catecholamine-secreting tumor in a Cushing's syndrome patient is contacted with a glucocorticoid receptor modulator, thereby treating Cushing's syndrome in the patient. For example, the methods disclosed herein include administering to a patient in need thereof, an effective amount of a glucocorticoid receptor modulator (GRM), such as a glucocorticoid receptor antagonist (GRA), thereby reducing the production of catecholamines by a tumor. For example, the methods disclosed herein include administering to a Cushing's syndrome patient an effective amount of a GRM, such as a GRA (such as, e.g., mifepristone), thereby treating Cushing's syndrome and reducing the production of catecholamines by a tumor. In embodiments, the tumor may be a metastatic or unresectable catecholamine-secreting tumor. In embodiments, the tumor may be a neuroendocrine tumor. The catecholamine-secreting tumor may be a pheochromocytoma, or may be a paraganglioma, or other tumor. In some cases, the catecholamine-secreting tumor may be a metastatic tumor; may be an unresectable nonmalignant tumor; or may be an unresectable, multifocal non-malignant tumor.

Applicant discloses herein methods of treating catecholamine-secreting tumors comprising administering compounds capable of modulating a glucocorticoid receptor (GR) and thereby providing beneficial therapeutic effects. In embodiments, the patient is a Cushing's syndrome patient, and the methods treat Cushing's syndrome in the patient. Embodiments of the methods include administering an effective amount of a glucocorticoid receptor modulator to a patient, wherein the patient is not simultaneously being administered an exogenous glucocorticoid receptor agonist. Embodiments of the methods include administering an effective amount of a glucocorticoid receptor modulator (GRM) to a patient, wherein the patient is i) not otherwise in need of treatment with a glucocorticoid receptor antagonist, and ii) is not simultaneously being administered an exogenous glucocorticoid receptor agonist. In embodiments, the glucocorticoid receptor modulators are glucocorticoid receptor antagonists (GRAs). In embodiments, the GRA is mifepristone.

In embodiments, beneficial therapeutic effects include reducing catecholamine excess in a patient with a catecholamine-secreting tumor; ameliorating the symptoms of catecholamine excess in a patient with a catecholamine-secreting tumor; improving the efficacy of alpha and beta-adrenergic receptor blockade in a patient with a catecholamine-secreting tumor; improving the therapeutic efficacy of somatostatin analogs in patients with catecholamine-secreting tumors; improving the efficacy of somatostatin analogs when used in imaging modalities; improving the efficacy of Peptide Receptor Radionuclide Therapy (PRRT) in patients with catecholamine-secreting tumors; and other therapeutic benefits.

In embodiments, beneficial therapeutic effects include treating Cushing's syndrome and reducing catecholamine excess in a Cushing's syndrome patient with a catecholamine-secreting tumor; treating Cushing's syndrome and ameliorating the symptoms of catecholamine excess in a Cushing's syndrome patient with a catecholamine-secreting tumor; treating Cushing's syndrome and improving the efficacy of alpha and beta-adrenergic receptor blockade in a Cushing's syndrome patient with a catecholamine-secreting tumor; treating Cushing's syndrome and improving the therapeutic efficacy of somatostatin analogs in a Cushing's syndrome patient with a catecholamine-secreting tumors; treating Cushing's syndrome and improving the efficacy of somatostatin analogs when used in imaging modalities in a Cushing's syndrome patient; treating Cushing's syndrome and improving the efficacy of Peptide Receptor Radionuclide Therapy (PRRT) in a Cushing's syndrome patient with a catecholamine-secreting tumor; and other therapeutic benefits.

In embodiments, the glucocorticoid receptor antagonist (GRA) may be a steroidal GRA, a GRA having a cyclohexyl-pyrimidine backbone; a GRA having a fused azadecalin backbone; a GRA having a heteroaryl ketone fused azadecalin backbone; or a GRA having an octahydro fused azadecalin backbone. In embodiments, the GRA is mifepristone.

The methods disclosed herein include methods of reducing the catecholamine production and tumor burden in a patient who has a metastatic or unresectable catecholamine-secreting tumor. The methods disclosed herein include methods of treating Cushing's syndrome and reducing the catecholamine production and tumor burden in a patient who has a metastatic or unresectable catecholamine-secreting tumor. In embodiments, the methods comprise administering an effective amount of a GRA at a daily dose of between 1 and 1000 mg/kg/day, or of between 1 and 500 mg/kg/day, or of between 0.1 and 200 mg/kg/day, or of between 0.1 and 100 mg/kg/day, or of between 0.1 and 50 mg/kg/day, or of between 0.1 and 20 mg/kg/day, or of between 0.1 and 15 mg/kg/day, or of between 0.1 and 10 mg/kg/day, or of between 0.1 and 5 mg/kg/day, or of between 0.1 and 3 mg/kg/day, for at least 5 weeks to a patient who has a metastatic or unresectable catecholamine-secreting tumor.

In embodiments, the GRA is mifepristone, and the methods comprise administering an effective amount of mifepristone at a daily dose of between 0.1 and 100 mg/kg/day, or of between 0.1 and 50 mg/kg/day, or of between 0.1 and 20 mg/kg/day, or of between 0.1 and 15 mg/kg/day, or of between 0.1 and 12 mg/kg/day, or of between 0.1 and 10 mg/kg/day, or of between 0.1 and 5 mg/kg/day, or of between 0.1 and 3 mg/kg/day, or of between 0.1 and 1 mg/kg/day, for at least 5 weeks to a patient who has a metastatic or unresectable catecholamine-secreting tumor. In embodiments, the patient is a Cushing's syndrome patient who has a metastatic or unresectable catecholamine-secreting tumor.

The methods disclosed herein include the use of a GRA as a monotherapy, and in combination with other therapeutic agents, to control catecholamine excess, to ameliorate the symptoms of catecholamine excess, or both, in a patient who has a catecholamine-secreting tumor. The methods disclosed herein include the use of a GRA as a monotherapy, and in combination with other therapeutic agents, a) to treat Cushing's syndrome and to control catecholamine excess, b) to treat Cushing's syndrome and to ameliorate the symptoms of catecholamine excess, or both, in a patient who has a catecholamine-secreting tumor. In embodiments, other therapeutics used in combination with GRAs include chemotherapy agents, adrenergic antagonists (e.g., alpha-adrenergic receptor antagonists, beta-adrenergic receptor antagonists, and antagonists having mixed alpha- and beta-adrenergic antagonist action), radiotherapy agents (e.g., compounds including a radioactive moiety, such as a peptide for use in Peptide Receptor Radionuclide Therapy (PRRT)), somatostatin, and somatostatin receptor agonists (e.g., somatostatin analogs) to control catecholamine excess, to ameliorate the symptoms of catecholamine excess, or both, in a patient, such as a Cushing's syndrome patient, who has a catecholamine-secreting tumor. In embodiments, somatostatin or somatostatin analogs are used in imaging (e.g., imaging of a tumor). In embodiments, the other agent may be administered in combination with, or administered concurrently with, or may be administered at different times than, the GRA.

In embodiments, Applicant provides methods of reducing catecholamine excess as discussed herein, with the proviso that the patient is not otherwise in need of treatment with a glucocorticoid receptor antagonist. In embodiments, Applicant provides methods of reducing catecholamine excess as discussed herein, with one or more further provisos selected from the group of further provisos consisting of i) the patient is not simultaneously being administered an exogenous estrogen receptor ligand; ii) the patient is not simultaneously being administered an exogenous selective androgen receptor modulator; iii) the patient is not simultaneously being administered an exogenous selective androgen receptor modulator; iv) the patient is not simultaneously being administered an exogenous D-homoandrosta-17-YL-carbamate derivative; and v) the patient is not simultaneously being administered an exogenous glucocorticoid receptor agonist.

In embodiments, a pharmaceutical composition consisting essentially of a GRA is administered to a patient, such as a Cushing's syndrome patient, who has a catecholamine-secreting tumor in an amount effective to reduce catecholamine secretion by the tumor, or in an amount effective to ameliorate the symptoms of catecholamine excess in the patient. In embodiments, a pharmaceutical composition consisting essentially of mifepristone is administered to a patient, such as a Cushing's syndrome patient, who has a catecholamine-secreting tumor in an amount effective to reduce catecholamine secretion by the tumor, or in an amount effective to ameliorate the symptoms of catecholamine excess in the patient.

In embodiments, a pharmaceutical composition comprising a GRA and another active agent is administered to a patient, such as a Cushing's syndrome patient, who has a catecholamine-secreting tumor in an amount effective to control catecholamine excess, to ameliorate the symptoms of catecholamine excess, or both, in the patient. In embodiments, the other active agents present in the pharmaceutical composition may include one or more of alpha-adrenergic receptor antagonists, beta-adrenergic receptor antagonists, somatostatin, and somatostatin analogs (e.g., somatostatin receptor agonists). In embodiments, the pharmaceutical composition comprises mifepristone and one or more of adrenergic antagonists (e.g., alpha-adrenergic receptor antagonists, beta-adrenergic receptor antagonists, and antagonists having mixed alpha- and beta-adrenergic antagonist action), somatostatin, and somatostatin analogs (e.g., somatostatin receptor agonists).

The methods and compositions disclosed herein provide improved methods and treatments for patients, such as Cushing's syndrome patients, suffering from catecholamine-secreting tumors.

DETAILED DESCRIPTION

Applicant provides definitions of some terms used in the present disclosure.

Definitions

The abbreviations used herein have their conventional meaning within the chemical and biological arts.

All ranges recited herein are inclusive ranges, wherein each range recited herein includes the lowest and highest doses of in the range. For example, the range "between 1 and 1000 mg/kg/day" includes doses of 1 mg/kg/day and doses of 1000 mg/kg/day.

As used herein, the term "binding" refers to persistent contact, or adherence (however brief or intermittent), between two compounds.

As used herein, the terms "affinity", "binding affinity", and related terms refer to the strength and specificity of binding, such as binding between a ligand and its receptor. "Higher affinity" is used with reference to comparative binding between two ligands to a receptor, where the ligand which binds with higher affinity binds at a lower concentration than does the "lower affinity" ligand. For example, in a competitive binding experiment, a high affinity ligand will compete with a reference ligand for binding to a receptor at a lower concentration than will the low affinity ligand compete for binding at the receptor.

The term "specific binding" refers to binding that is more selective, and typically stronger, than mere non-specific adhesion between compounds. Specific binding may be exemplified by the binding which occurs between a ligand and its receptor.

A "binding constant" may be used to refer to a measure of the specificity of binding. Constants which provide useful information regarding the strength and specificity of binding include the equilibrium dissociation constant $K_d$ and its inverse, the equilibrium association constant (or affinity constant) $K_a$.

As used herein, the term "inhibition constant" refers to $K_i$, which is similar to the equilibrium dissociation constant $K_d$ for simple, reversible inhibitors. Inhibition of binding between a ligand its receptor, or inhibition of action which results from binding between a ligand its receptor, may take many forms, including competitive inhibition, uncompetitive inhibition, and non-competitive inhibition. Inhibition constants are expressed in units of concentration, with an inhibitor having a $K_i$, in the nanomolar (nm) range being a more effective inhibitor than an inhibitor having a $K_i$, in the micromolar (μm) range. When the inhibitory actions of two inhibitors are compared, for example, an inhibitor having a $K_i$, in the nm range would be termed the "stronger inhibitor", and an inhibitor $K_i$, in the μm range would be termed the "weaker inhibitor". Similarly, the inhibitor having a $K_i$, in the nm range would be termed a "strong inhibitor", and the inhibitor $K_i$, in the μm range would be termed a "weak inhibitor".

"Patient" or "subject in need thereof" refers to a person having, or suspected of having, a catecholamine-secreting tumor, a neuroendocrine tumor, or a catecholamine-secreting neuroendocrine tumor. A catecholamine-secreting tumor can be identified and/or monitored by detection of the tumor, detection of elevated levels of catecholamine, detection of symptoms caused by a catecholamine-secreting tumor, and combinations thereof. A neuroendocrine tumor can be detected and/or monitored by detection of the tumor or detection of symptoms caused by the tumor.

As used herein, the terms "catecholamine" and "catecholamines" are used as understood by those of skill in the medical arts, and refer to small molecules including dopamine, norepinephrine, and epinephrine (adrenaline).

"Treat", "treating" and "treatment" refer to any indicia of success in the treatment or amelioration of a pathology or condition, including any objective or subjective parameter such as abatement; remission; diminishing of symptoms or making the pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters; including the results of a physical examination; histopathological examination (e.g., analysis of biopsied tissue); laboratory analysis of urine, saliva, tissue samples, serum, plasma, or blood (e.g., to detect cortisol or catecholamine levels); or imaging (e.g., imaging of a catecholamine-secreting tumor or of detectably labeled somatostatin analogs). Effective treatment refers to a reduction in catecholamine production, catecholamine-secretion, a reduction in catecholamine or cortisol levels in the blood of the patient, a reduction in catecholamine-secreting tumor burden (e.g., catecholamine-secreting tumor size, mass, volume, viability, or proliferation), or an increase in tumor cell death in the catecholamine-secreting tumor.

As used herein, administration "with or soon after a meal" means that a therapeutic composition is administered with a meal, or within about 30 minutes after a patient begins consuming a meal.

As used herein, the term "simultaneously or sequentially administering" refers to administration of a GRM, such as a GRA, compound and somatostatin receptor ligand compound (e.g., somatostatin or somatostatin analog (SSA))

such that the two compounds are in the body at the same time in amounts effective to treat a catecholamine-secreting tumor.

As used herein, the term "effective amount," "amounts effective," or "therapeutically effective amount" refers to an amount or amounts of one or more pharmacological agents effective to treat, eliminate, or mitigate at least one symptom of the disease being treated. In some cases, "effective amount," "amounts effective," or "therapeutically effective amount" can refer to an amount of a functional agent or of a pharmaceutical composition useful for exhibiting a detectable therapeutic or inhibitory effect. The effect can be detected by any assay method known in the art. In some cases, the amounts effective, or the like, refer to amounts effective to reduce catecholamine levels. In some cases, the amounts effective, or the like, refer to amounts effective to reduce cortisol (e.g., serum cortisol, salivary cortisol, or urinary free cortisol) levels. In some cases, the amounts effective, or the like, refer to amounts effective to reduce catecholamine levels or cortisol levels, or a combination thereof, by at least 10%, 20%, 30%, 40%, 50%, 60%, 75%, 90%, 99%, or more.

As used herein, the terms "effective to reduce catecholamine production", "effective to reduce secretion of catecholamine", and the like refer to a method, treatment, composition, or amount that can reduce the production and/or secretion of a catecholamine or catecholamines by neuroendocrine or other tumors as compared to the production and/or secretion of a catecholamine or catecholamines by such a tumor in the absence of the method, treatment, composition, or amount.

As used herein, the term "catecholamine-secreting tumor" refers to an adenoma, adenocarcinoma, neuroendocrine, pituitary, or other tumor that produces catecholamines. In general, a catecholamine-secreting tumor will also secrete catecholamines. In some cases, the catecholamine-secreting tumor can cause an increase in blood, plasma, or serum levels of catecholamines or blood, plasma, serum, or urinary (e.g., urinary free) catecholamine levels in a subject having the catecholamine-secreting tumor as compared to a subject that does not have a catecholamine-secreting tumor. A catecholamine-secreting (e.g., a catecholamine-secreting) tumor may typically be a neuroendocrine tumor (NET) which produces and/or secretes catecholamines.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, sodium chloride (NaCl), normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

As used herein, the terms "steroid" and "steroids", and the phrase "steroidal backbone" in the context of glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

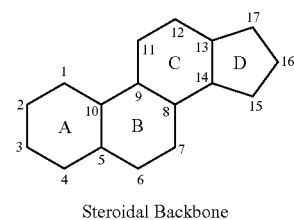

Formula I

Steroidal Backbone

The two most commonly known classes of structural modifications of the cortisol steroid backbone to create glucocorticoid antagonists include modifications of the 11-β hydroxy group and modification of the 17-β side chain (See, e. g., Lefebvre (1989) J. Steroid Biochem. 33: 557-563).

As used herein, the terms "progesterone receptor" and "PR" refer to a naturally occurring receptor which binds progesterone.

The term "aldosterone" refers to the naturally occurring mineralocorticoid hormone having the structure:

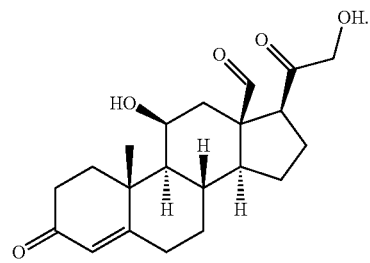

A mineralocorticoid receptor (MR), also known as a type I glucocorticoid receptor (GR I), is activated by aldosterone in humans.

The term "cortisol" refers to the naturally occurring glucocorticoid hormone (also known as hydrocortisone) having the structure:

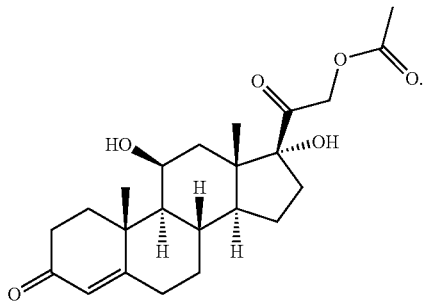

As used herein, the term glucocorticoid receptor (GR) refers to a receptor that binds a glucocorticoid, such as cortisol, dexamethasone, or other molecules. A glucocorticoid receptor, also known as a corticosteroid receptor or as a type II glucocorticoid receptor (GR II), and in humans, as a cortisol receptor, is activated by cortisol in humans (or, e.g., by corticosterone ("cortisone") in some other animals, such as rats and mice). The human cortisol receptor (GR II receptor, Genbank: P04150) specifically binds to cortisol and/or cortisol analogs (e.g. dexamethasone). The term includes isoforms of GR II, recombinant GRII, and mutated GRII.

As used herein, the term glucocorticoid receptor modulator (GRM) refers to an agent that affects the action of a glucocorticoid receptor (GR). Such modulation may include activation (agonist action), partial activation (partial agonist action), inhibition (reduction in activation of the receptor under conditions where it would otherwise be activated, such as in the presence of cortisol), and blockade (complete or near complete suppression of activation of the receptor under conditions where it would otherwise be activated, such as in the presence of cortisol). GRMs may affect the activity of a GR by increasing or by decreasing the activity of the GR. GRMs include steroids, and, in embodiments, include pyrimidinediones; azadecalins; fused-ring azadecalins; heteroaryl-ketone fused-ring azadecalins; and other compounds.

As used herein, the terms "glucocorticoid agonist", "glucocorticoid receptor agonist", "glucocorticoid receptor type II agonist", and "GRII agonist" refer to a compound or agent which may bind to and activate a cortisol receptor. Such agents include, for example, cortisol, dexamethasone, prednisone, and other compounds and agents which bind to and activate a GRII.

As used herein, the terms "glucocorticoid antagonist", "glucocorticoid receptor antagonist", "glucocorticoid antagonist", "glucocorticoid receptor type II antagonist", "GRII antagonist", and "GRA" refer to agents that inhibit the action of a cortisol receptor; such inhibition may include interfering with the binding of a glucocorticoid agonist such as cortisol, dexamethasone, or other compound or agent which may bind to and activate a cortisol receptor. A GRA is a glucocorticoid receptor modulator. Inhibition constants ($K_i$) for GRAs against the human cortisol receptor may be between about 0.0001 nM and about 1,000 nM; preferably may be between about 0.0005 nM and about 10 nM, and most preferably between about 0.001 nM and about 1 nM. Thus, the terms "glucocorticoid receptor antagonist" and "GRA" refer to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," we intend the drug to preferentially bind to the GR rather than another nuclear receptors, such as mineralocorticoid receptor (MR) or progesterone receptor (PR).

By "specific," the drug preferentially binds to the GR rather than other nuclear receptors, such as mineralocorticoid receptor (MR), androgen receptor (AR), or progesterone receptor (PR). It is preferred that the specific glucocorticoid receptor antagonist bind GR with an affinity that is 10× greater ($\frac{1}{10}^{th}$ the $K_d$ value) than its affinity to the MR, AR, or PR. In a more preferred embodiment, the specific glucocorticoid receptor antagonist binds GR with an affinity that is 100× greater ($\frac{1}{100}^{th}$ the $K_d$ value) than its affinity to the MR, AR, or PR.

As used herein, "mifepristone" refers to a GRA which binds to GRII (and which also binds to a progesterone receptor). Mifepristone (11β-(4-dimethylaminophenyl)-17β-hydroxy-17α-(1-propynyl)-estra-4,9-dien-3-one) has the structure:

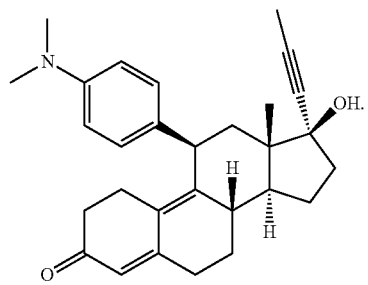

Mifepristone is also referred to as, e.g., RU486, as RU38.486, and as 17-beta-hydroxy-11-beta-(4-dimethylaminophenyl)-17-alpha-(1-propynyl)-estra-4,9-dien-3-one).

As used herein, "RU28362" refers to the glucocorticoid receptor agonist 11,17-dihydroxy-6-methyl-17-(1-propynyl) androsta-1,4,6-triene-3-one].

As used herein, the phrase "non-steroidal backbone" in the context of glucocorticoid receptor antagonists containing such refers to glucocorticoid receptor antagonists that do not share structural homology to, or are not modifications of, cortisol. Such compounds include synthetic mimetics and analogs of proteins, including partially peptidic, pseudopeptidic and non-peptidic molecular entities.

Non-steroidal GRA compounds also include GRAs having a cyclohexyl-pyrimidine backbone, a fused azadecalin backbone, a heteroaryl ketone fused azadecalin backbone, or an octahydro fused azadecalin backbone. Exemplary GRAs having a cyclohexyl-pyrimidine backbone include those described in U.S. Pat. No. 8,685,973. Exemplary GRAs having a fused azadecalin backbone include those described in U.S. Pat. Nos. 7,928,237; and 8,461,172. Exemplary GRAs having a heteroaryl ketone fused azadecalin backbone include those described in U.S. Pat. No. 8,859,774. Exemplary GRAs having an octohydro fused azadecalin backbone include those described in U.S. Patent Application Publication 2015-0148341.

Description of compounds useful in the methods disclosed herein, and suitable for the pharmaceutical compositions disclosed herein are described in accordance with principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, N-oxide, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S or N.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

As used herein, the term "chemotherapy" refers to medical treatments typically used to treat cancer. Chemotherapy treatments include the use of agents which are toxic to cancerous tissues and cells, or which act to slow or reduce the growth or spread of cancerous tissues and cells. Chemotherapy agents include antineoplastic agents and may be derived from natural compounds (e.g., taxols); may be, may mimic, or may reduce or block the actions of naturally occurring hormones, growth factors, or immunologically active molecules; may be synthetic small molecules; may be antibodies or antibody conjugates; and may be other agents. Exemplary chemotherapy agents include, but are not limited to, taxanes, taxol, docetaxel, paclitaxel, actinomycin, anthracyclines, doxorubicin, daunorubicin, valrubicin, bleomycin, cisplatin, trastuzumab (Herceptin®), trastuzumab emtansine (Kadcyla®), imatinib (Gleevec®), eribulin (Halaven®), among others known in the art.

As used herein, the terms "pharmaceutical composition" and "formulation" refer to compositions suitable for administration to a patient for treatment of a medical condition or for amelioration of symptoms of a medical condition. A pharmaceutical composition includes an active ingredient (e.g., a GRA; or a combination of a GRA and another active agent, such as, e.g., an adrenergic antagonist, or somatostatin, or a somatostatin analog) and a pharmaceutically acceptable excipient. In embodiments, a pharmaceutical composition includes one or more active ingredients and one or more pharmaceutically acceptable excipients.

As used herein, the term "pharmaceutically acceptable excipient" refers to a substance that aids the administration of an active agent to and absorption by a subject and can be included in pharmaceutical compositions without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

As used herein, the terms "sustained release," "slow release," "long acting," "prolonged release," and the like refer to a pharmaceutical composition or formulation containing at least one active ingredient (e.g., GRA, adrenergic antagonist, somatostatin, somatostatin analog, or combination thereof) formulated to maintain a therapeutic concentration of active ingredient(s) in a patient for a longer period of time in comparison to formulations that are not designed for such sustained release. In some cases, the sustained release formulation maintains therapeutic concentration of one or more active ingredient(s) for, or for at least, one week, two weeks, three weeks, four weeks, five weeks, or six weeks. In some cases, the sustained release formulation is administered to a patient every one, two, three, four, five, or six weeks. Examples of commercially available sustained release formulations include, but are not limited to, sustained release formulations of the somatostatin analogs octreotide LAR, prolonged release lanreotide, and lanreotide autogel.

As used herein, the term "adrenergic receptor" refers to naturally occurring receptors which bind adrenergic compounds such as catecholamines (e.g., dopamine, norepinephrine, and epinephrine). Adrenergic receptors may be one of several subtypes, including one of two general subtypes, termed "alpha-adrenergic receptors" and "beta-adrenergic receptors". The binding and actions of adrenergic agonists, and the binding and effects of adrenergic antagonists, may differ between alpha-adrenergic receptors and beta-adrenergic receptors. Alpha-adrenergic receptor agonists (e.g., sympathomimetics) include, for example, phenylephrine, guanethidine, and other compounds. Beta-adrenergic receptor agonists (e.g., beta agonists) include, for example, isoproterenol and isoprenaline.

As used herein, the term "adrenergic antagonist" refers to a compound that reduces the activation of adrenergic receptors, and includes, for example, alpha-adrenergic receptor antagonists, beta-adrenergic receptor antagonists, and antagonists having mixed alpha- and beta-adrenergic antagonist action. Alpha-adrenergic receptor antagonists (e.g., alpha blockers) include, for example, phentolamine, prazosin, and yohimbine. Beta-adrenergic receptor antagonists (e.g., beta blockers) include, for example, propranolol, timolol, and esmolol.

As used herein, "somatostatin" and "SST" refer to a naturally occurring peptide hormone, in any of its forms, also known as "growth hormone inhibiting hormone (or "factor")", "growth hormone release inhibiting hormone (or "factor")", "somatotropin-release inhibiting hormone (or "factor")", or other names, as understood by those of skill in the art. Human somatostatin is described at Uniprot P61278. Somatostatin occurs and acts (e.g., by reducing or blocking the release of growth hormone (somatotropin)) in at least two forms, a long form (e.g., 28 amino acids in humans) and a short form (e.g., 14 amino acids in humans). Thus, somatostatin is an inhibitory polypeptide with two primary biologically active forms SST14 and SST28. In some cases, the ligand is a pre- or pre-pro form of somatostatin, or an analog thereof.

As used herein, the term somatostatin receptor refers to a class of G-protein coupled seven transmembrane receptors that bind somatostatin. Five somatostatin receptor sub-types are known, and are referred to as SSTR1-SSTR5 respectively.

As used herein, the terms "somatostatin receptor ligand," or "somatostatin ligand analog" or "somatostatin analog" refer to any ligand of any one of the somatostatin receptor subtypes (SSTR1-SSTR5). A "somatostatin analog" mimics, at least in part, the action of somatostatin. Examples of somatostatin analogs include, but are not limited to, pasireotide, octreotate, octreotide, lanreotide, and derivatives thereof, including, for example, labeled (such as, e.g., radiolabeled, and detectably labeled) derivatives thereof.

In some cases, the somatostatin receptor ligand is somatostatin. In some cases, the somatostatin ligand is a somatostatin analog. In preferred embodiments, a somatostatin analog is an agonist of a somatostatin receptor. In some cases, the somatostatin ligand preferentially binds or activates somatostatin receptor type 2 (SSTR2). In some cases, the somatostatin receptor ligand preferentially binds or activates somatostatin receptor type 5 (SSTR5). In some cases, the somatostatin receptor ligand preferentially binds or activates SSTR2 and SSTR5. In some cases, the somatostatin receptor ligand preferentially binds or activates SSTR2, SSTR3, and SSTR5. The somatostatin receptor ligand can be provided or administered in a long acting, prolonged, or slow release formulation.

Exemplary somatostatin receptor ligands include, without limitation, peptide somatostatin receptor ligands, such as those described in U.S. Pat. No. 8,946,154. Exemplary somatostatin receptor ligands further include, without limitation, somatostatin polypeptides from *Oncorhynchus mykiss* and analogs or derivatives thereof, such as those described in U.S. Pat. No. 6,818,739. Exemplary somatostatin receptor ligands further include, without limitation, antibodies that bind to, or bind to and activate one or more somatostatin receptor subtypes (e.g., any one of SSTR1-5, or a combination thereof). Exemplary somatostatin receptor ligands further include, without limitation, non-peptide somatostatin receptor ligands such as those described in U.S. Pat. No. 7,189,856. Exemplary somatostatin receptor ligands further include, without limitation, the somatostatin receptor ligands described in U.S. Pat. No. 6,358,941.

Exemplary somatostatin receptor ligands further include, without limitation, selective somatostatin receptor ligands. For example, the somatostatin receptor ligand can be selective for (e.g., selectively binds to, or selectively activates) one of SSTR1-5. In some cases, the somatostatin receptor ligand is selective for (e.g., selectively binds to, or selectively activates) SSTR1. In some cases, the somatostatin receptor ligand is selective for SSTR2. Exemplary In some cases, the somatostatin receptor ligand is selective for (e.g., selectively binds to, or selectively activates) SSTR3. In some cases, the somatostatin receptor ligand is selective for (e.g., selectively binds to, or selectively activates) SSTR4. In some cases, the somatostatin receptor ligand is selective for (e.g., selectively binds to, or selectively activates) SSTR5.

In some cases, the somatostatin receptor ligand is selective for (e.g., selectively binds to, or selectively activates) two somatostatin receptors selected from the group consisting of SSTR1-5. For example, the somatostatin receptor ligand can be selective for SSTR1 and 4. As another example, the somatostatin receptor ligand can be selective for SSTR2 and 5. In some cases, the somatostatin receptor ligand is selective for (e.g., selectively binds to, or selectively activates) three somatostatin receptors selected from the group consisting of SSTR1-5. In some cases, the somatostatin receptor ligand is selective for (e.g., selectively binds to, or selectively activates) four somatostatin receptors selected from the group consisting of SSTR1-5. Exemplary selective somatostatin receptor ligands include, without limitation, those described in Rohrer et al., 1998, Science 282:737. Exemplary selective somatostatin receptor ligands further include, without limitation, those described in U.S. Patent Appl. Pub. No. 2006/0089299.

In some cases, the somatostatin receptor ligand is selected from the group consisting of octreotide, $^{111}$In-octreotide, octreotate, pasireotide, lanreotide, and analogs or derivatives thereof. In some cases, the somatostatin receptor ligand is coupled to a detectable label or a cytotoxic agent. Exemplary detectable labels include spin labels, fluorescent labels, and radionuclides. Exemplary cytotoxic agents include radionuclides and cytotoxic chemotherapeutics.

As used herein, the term "somatostatin imaging" refers to methods of imaging in which somatostatin, or a somatostatin analog, is labeled (e.g., bound with a radioactive, fluorescent or other detectable element or compound), administered to a subject, and the label detected. Detection of the label is useful, for example, for determining the location of somatostatin receptors in a subject, and may be particularly useful for determining ectopic or otherwise inappropriate locations of somatostatin receptors in a subject.

In some embodiments, the method comprises administering a somatostatin analog (SSA). In some cases, the somatostatin analog is selected from the group consisting of octreotide, octreotate, pasireotide, lanreotide, and derivatives thereof. In some cases, the somatostatin analog is radiolabeled. In some cases, the radiolabeled somatostatin analog is radiolabeled with a label suitable for imaging, such as, e.g., $^{111}$In or $^{123}$I. In some cases, the somatostatin analog is radiolabeled with a label suitable for radionuclide therapy, such as, e.g., $^{111}$In, $^{131}$I, $^{90}$Y, $^{177}$Lu, or $^{213}$Bi. In some cases, the therapeutic radionuclide is selected from the group consisting of $^{111}$In, $^{90}$Y, $^{177}$Lu, and $^{213}$Bi. In some cases, the therapeutic radionuclide is selected from the group consisting of $^{90}$Y, $^{177}$Lu, and $^{213}$Bi. In some cases, the somatostatin analog is labeled with a radionuclide selected from the group consisting of $^{32}$P, $^{45}$Ti, $^{48}$V, $^{49}$V, $^{59}$Fe, $^{60}$Cu, $^{61}$Cu, $^{62}$Cu, $^{64}$Cu, $^{65}$Zn, $^{67}$Cu, $^{67}$Ga, $^{68}$Ga, $^{71}$As, $^{72}$As, $^{76}$As, $^{76}$Br, $^{77}$As, $^{89}$Sr, $^{90}$Y, $^{99m}$Tc, $^{111}$In, $^{117m}$Sn, $^{123}$I, $^{125}$I, $^{131}$I, $^{149}$Pm, $^{153}$Gd, $^{153}$Pm, $^{153}$Sm, $^{166}$Ho, $^{177}$Lu, $^{186}$Re, $^{188}$Re, $^{201}$Tl, $^{203}$Pb, $^{209}$Pb, $^{209}$Bi, $^{211}$At, $^{212}$Bi, $^{212}$Pb, $^{213}$Bi, $^{223}$Ra, and $^{225}$Ac. In some cases, the somatostatin analog is $^{123}$I-Tyr$^3$-octreotide, $^{111}$In-DTPA-D-Phe$^1$-octreotide, [$^{111}$In-DTPA$^0$]octreotide, [$^{90}$Y-DOTA, Tyr$^3$]octreotide, or [$^{177}$Lu-DOTA, Tyr$^3$]octreotate. In some cases, the subject in need thereof suffers from inoperable or metastatic catecholamine-secreting tumor, or an inoperable and metastatic catecholamine-secreting tumor. In some cases, the inoperable and/or metastatic catecholamine-secreting tumor is a neuroendocrine tumor.

In some cases, the somatostatin analog is administered in a sustained release formulation. In some cases, the somatostatin analog is administered as octreotide LAR, lanreotide PR, or lanreotide autogel.

As used herein, the phrase "Peptide receptor radionuclide therapy" or its acronym "PRRT" refer to therapeutic interventions in which a ligand is made radioactive by binding to it a radioactive element or compound, and is administered to a subject in order that the radioactive ligand bind to its receptor to deliver therapeutic doses of radiation. PRRT may be effective in cases where a tumor inappropriately expresses, or overexpresses, a receptor for which a radioactive ligand may be provided. In embodiments where a tumor inappropriately expresses, or overexpresses, a somatostatin receptor, radiolabeled somatostatin, or a radiolabeled somatostatin analog, may be administered to a patient.

Treatment Methods

Methods disclosed herein include methods of treating tumors, such as catecholamine-secreting tumors, comprising administering compounds capable of modulating a glucocorticoid receptor (GR) and thereby providing beneficial therapeutic effects. In embodiments, the patient having the catecholamine-secreting tumor is a Cushing's syndrome patient, and the methods treat Cushing's syndrome in the patient. For example, methods disclosed herein include administering to a patient in need thereof an effective amount of a glucocorticoid receptor modulator (GRM), such as a glucocorticoid receptor antagonist (GRA), thereby reducing the production of catecholamines by a tumor. In embodiments, the disclosed methods include administering to a Cushing's syndrome patient having a tumor an effective amount of a glucocorticoid receptor modulator (GRM), such as a glucocorticoid receptor antagonist (GRA), thereby reducing the production of catecholamines by the tumor, and thereby treating Cushing's syndrome. In embodiments, the tumor may be a neuroendocrine tumor.

Embodiments of the methods include administering an effective amount of a glucocorticoid receptor modulator to a patient, wherein the patient is not simultaneously being administered an exogenous glucocorticoid receptor agonist. Embodiments of the methods include administering an effective amount of a glucocorticoid receptor modulator to a patient, wherein the patient is i) not otherwise in need of treatment with a glucocorticoid receptor modulator, and ii) is not simultaneously being administered an exogenous glucocorticoid receptor agonist. In embodiments, the GR modulator is a glucocorticoid receptor antagonist (GRA). Accordingly, in embodiments, the methods include administering an effective amount of a GRA to a patient, wherein the patient is i) not otherwise in need of treatment with a GRA, and ii) is not simultaneously being administered an exogenous glucocorticoid receptor agonist.

GRA compounds may be administered with, concurrently with, or closely in time with, other treatments or pharmaceutical agents. Other treatments or pharmaceutical agents may include, for example, chemotherapy agents, alpha-adrenergic receptor antagonists, beta-adrenergic receptor antagonists, radiotherapy agents (e.g., compounds including a radioactive moiety, such as a peptide for use in Peptide Receptor Radionuclide Therapy (PRRT)), somatostatin, and somatostatin receptor agonists (e.g., somatostatin analogs). In embodiments, GRA compounds may be administered in pharmaceutical compositions also including another active agent, where the other active agent may be one of more of an adrenergic antagonist, somatostatin, and a somatostatin analog.

For example, administration of a GRA effective to decrease the activity of cortisol in combination with adrenergic antagonists could act synergistically with adrenergic antagonists administered to treat a neuroendocrine tumor improve the efficacy of such adrenergic antagonist treatment. In embodiments, the neuroendocrine tumor is in a Cushing's syndrome patient, and the methods treat Cushing's syndrome in the patient. In a further example, increased cortisol activity at the tumor level could affect the expression of somatostatin receptors such as sst2 and as a result could affect the efficacy of somatostatin or of somatostatin analogs. Thus, administration of a GRA effective to decrease the activity of cortisol at the tumor level could improve the efficacy of somatostatin or somatostatin analogs administered to treat a neuroendocrine tumor. Other concomitant actions and synergistic activities resulting from administration of a GRM (such as a GRA) along with or closely in time with administration of other agents, such as chemotherapy agents, alpha-adrenergic receptor antagonists, beta-adrenergic receptor antagonists, radiotherapy agents, somatostatin, and somatostatin receptor agonists (e.g., somatostatin analogs) could improve the efficacy of methods for treating a neuroendocrine tumor as compared to methods in which such other agents are used in the absence of a GRM (such as a GRA).

In embodiments, beneficial therapeutic effects include reducing catecholamine excess in a patient with a catecholamine-secreting tumor; ameliorating the symptoms of catecholamine excess in a patient with a catecholamine-secreting tumor; improving the efficacy of alpha and beta-adrenergic receptor blockade in a patient with a catecholamine-secreting tumor; improving the therapeutic efficacy of somatostatin analogs in patients with catecholamine-secreting tumors; improving the efficacy of somatostatin analogs when used in imaging modalities; improving the efficacy of Peptide Receptor Radionuclide Therapy (PRRT) in patients with catecholamine-secreting tumors; and other therapeutic benefits. In embodiments, the beneficial therapeutic effects include treating Cushing's syndrome in a Cushing's syndrome patient with a catecholamine-secreting tumor.

In embodiments, the glucocorticoid receptor modulator is a glucocorticoid receptor antagonist (GRA). In embodiments, the GRA is an antagonist of a glucocorticoid type II (GRII) receptor. In embodiments, the GRA binds preferentially to a GRII receptor as compared to its binding to a glucocorticoid type I (GRI) receptor. In embodiments, the GRA reduces the activation of a GRII receptor. In embodiments, the GRA reduces the activity of a GRII receptor. In embodiments, the GRA may bind to a progesterone receptor (PR), and may bind to a glucocorticoid receptor with higher affinity than it binds to PR. In embodiments, the GRA is mifepristone. In embodiments, the GRA is a selective inhibitor of the glucocorticoid receptor. In embodiments, the GRA may only poorly bind to PR, or may not measurably bind to PR.

In some embodiments, the GRA comprises a steroidal backbone with at least one phenyl-containing moiety in the 11-β position of the steroidal backbone. In some cases, the phenyl-containing moiety in the 11-β position of the steroidal backbone is a dimethylaminophenyl moiety. In some cases, the GRA is mifepristone. In some embodiments, the GRA is selected from the group consisting of 11β-(4-dimethylaminoethoxyphenyl)-17α-propynyl-17β-hydroxy-4,9 estradien-3-one and (17α)-17-hydroxy-19-(4-methylphenyl)androsta-4,9(11)-dien-3-one. In some embodiments, the GRA is (11β,17β)-11-(1,3-benzodioxol-5-yl)-17-hydroxy-17-(1-propynyl)estra-4,9-dien-3-one.

In embodiments, the GRAs include compounds having a cyclohexyl-pyrimidine backbone; (GRAs) having a fused azadecalin backbone; (GRAs) having a heteroaryl ketone fused azadecalin backbone; and (GRAs) having an octahydro fused azadecalin backbone.

In some embodiments, the GRA has a non-steroidal backbone. In some cases, the glucocorticoid receptor antagonist backbone is a cyclohexyl pyrimidine. In some cases, wherein the cyclohexyl pyrimidine has the following formula:

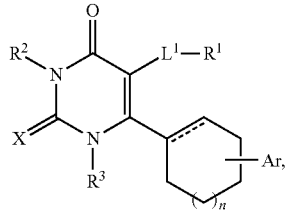

wherein the dashed line is absent or a bond; X is selected from the group consisting of O and S; $R^1$ is selected from the group consisting of cycloalkyl, heterocycloalkyl, aryl and heteroaryl, optionally substituted with from 1 to 3 $R^{1a}$ groups; each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl $OR^{1b}$, halogen, $C_{1-6}$ haloalkyl, $C_{1-6}$ haloaloxy, $OR^{1b}$, $NR^{1b}R^{1c}$, $C(O)R^{1b}$, $C(O)OR^{1b}$, $OC(O)R^{1b}$, $C(O)NR^{1b}R^{1c}$, $NR^{1b}C(O)R^{1c}$, $SO_2R^{1b}$, $SO_2NR^{1b}R^{1c}$, cycloalkyl, heterocycloalkyl, aryl and heteroaryl; $R^{1b}$ and $R^{1c}$ are each independently selected from the group consisting of H and $C_{1-6}$ alkyl; $R^2$ is selected from the group consisting of H, $C_{1-6}$ alkyl, $C_{1-6}$ alkyl-$OR^{1b}$, $C_{1-6}$ alkyl $NR^{1b}R^{1c}$ and $C_{1-6}$ alkylene heterocycloalkyl; $R^3$ is selected from the group consisting of H and $C_{1-6}$ alkyl; Ar is aryl, optionally substituted with 1-4 $R^4$ groups; each $R^4$ is independently selected from the group consisting of H, $C_{1-6}$ alkyl, $C_{1-6}$ alkoxy, halogen, $C_{1-6}$ haloalkyl and $C_{1-6}$ haloalkoxy; $L^1$ is a bond or $C_{1-6}$ alkylene; and subscript n is an integer from 0 to 3, or salts and isomers thereof.

In some cases, the GRA having a non-steroidal backbone is a fused azadecalin. In some cases, the fused azadecalin is a compound having the following formula:

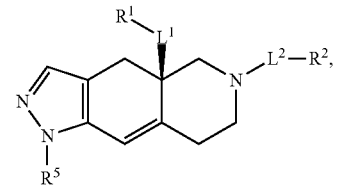

wherein $L^1$ and $L^2$ are members independently selected from a bond and unsubstituted alkylene; $R^1$ is a member selected from unsubstituted alkyl, unsubstituted heteroalkyl, unsubstituted heterocycloalkyl, —$OR^{1A}$, $NR^{1C}R^{1D}$, —$C(O)NR^{1C}R^{1D}$, and —$C(O)OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen; $R^2$ has the formula:

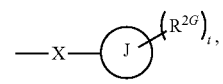

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$; J is phenyl; t is an integer from 0 to 5; X is —$S(O_2)$—; and $R^5$ is phenyl optionally substituted with 1-5 $R^{5A}$ groups, wherein $R^{5A}$ is a member selected from hydrogen, halogen, —$OR^{5A1}$, $S(O_2)NR^{5A2}R^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, or salts and isomers thereof.

In some cases, the GRA having a non-steroidal backbone is a heteroaryl ketone fused azadecalin or an octahydro fused azadecalin. In some cases, the heteroaryl ketone fused azadecalin has the formula:

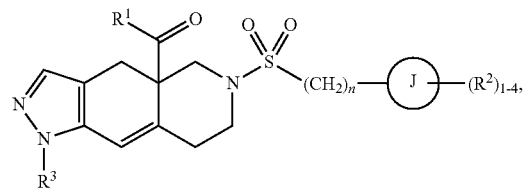

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, CN, N-oxide, $C_{3-8}$ cycloalkyl, and $C_{3-8}$ heterocycloalkyl; ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2A}$, $S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups; alternatively, two $R^2$ groups linked to the same carbon are combined to form an oxo group (=O); alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups; $R^{2a}$ and $R^{2b}$ are each independently selected from the group consisting of hydrogen and $C_{1-6}$ alkyl; each $R^{2c}$ is independently selected from the group consisting of hydrogen, halogen, hydroxy, $C_{1-6}$ alkoxy, $C_{1-6}$ haloalkoxy, CN, and $NR^{2a}R^{2b}$; each $R^{2d}$ is independently selected from the group consisting of hydrogen and $C_{1-6}$ alkyl, or two $R^{2d}$ groups attached to the same ring atom are combined to form (=O); $R^3$ is selected from the group consisting of phenyl and pyridyl, each optionally substituted with 1-4 $R^{3a}$ groups; each $R^{3a}$ is independently selected from the group consisting of hydrogen, halogen, and $C_{1-6}$ haloalkyl; and subscript n is an integer from 0 to 3; or salts and isomers thereof.

In some cases, the octahydro fused azadecalin has the formula:

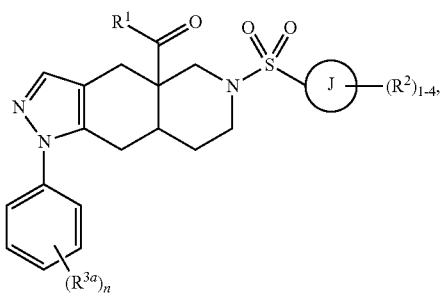

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl; ring J is selected from the group consisting of an aryl ring and a heteroaryl ring having from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O and S; alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups; $R^{2a}$, $R^{2b}$ and $R^{2c}$ are each independently selected from the group consisting of hydrogen and $C_{1-6}$ alkyl; each $R^{3a}$ is independently halogen; and subscript n is an integer from 0 to 3, or salts and isomers thereof.

In embodiments, the methods disclosed herein provide a method of reducing the catecholamine production and tumor burden in a patient who has a metastatic or unresectable catecholamine-secreting tumor, the method comprising administering an effective amount of a GRA at a daily dose of between 1 and 1000 mg/kg/day for at least 5 weeks with the proviso that: i) the patient is not otherwise in need of treatment with a glucocorticoid receptor antagonist, and ii) the patient is not simultaneously being administered an exogenous glucocorticoid receptor agonist. In embodiments of such methods of reducing the catecholamine production and tumor burden in a patient who has a metastatic or unresectable catecholamine-secreting tumor, an effective amount of a GRA is administered at a daily dose of between 1 and 1000 mg/kg/day, or of between 1 and 500 mg/kg/day, or of between 0.1 and 200 mg/kg/day, or of between 0.1 and 100 mg/kg/day, or of between 0.1 and 50 mg/kg/day, or of between 0.1 and 20 mg/kg/day, or of between 0.1 and 15 mg/kg/day, or of between 0.1 and 10 mg/kg/day, or of between 0.1 and 5 mg/kg/day, or of between 0.1 and 3 mg/kg/day, for at least 5 weeks, with the same proviso. In embodiments, the metastatic or unresectable catecholamine-secreting tumor is in a Cushing's syndrome patient, and the administration of a GRA treats Cushing's syndrome in the patient. In embodiments, the GRA is administered once daily. In embodiments, the GRA is administered once daily with or soon after a meal.

In embodiments, the GRA is mifepristone, and the methods comprise administering an effective amount of mifepristone at a daily dose of between 0.1 and 100 mg/kg/day, or of between 0.1 and 50 mg/kg/day, or of between 0.1 and 20 mg/kg/day, or of between 0.1 and 15 mg/kg/day, or of between 0.1 and 12 mg/kg/day, or of between 0.1 and 10 mg/kg/day, or of between 0.1 and 5 mg/kg/day, or of between 0.1 and 3 mg/kg/day, or of between 0.1 and 1 mg/kg/day, for at least 5 weeks, with the same proviso.

In embodiments, a GRA is used as a monotherapy to control catecholamine excess, to ameliorate the symptoms of catecholamine excess, or both, in a patient who has a catecholamine-secreting tumor. In embodiments, a GRA is used as a monotherapy to treat Cushing's syndrome, to control catecholamine excess, to ameliorate the symptoms of catecholamine excess, or all three, in a patient who has a catecholamine-secreting tumor. In embodiments, a GRA is used in combination with chemotherapy to control catecholamine excess, to ameliorate the symptoms of catecholamine excess, to treat Cushing's syndrome, or all three, in a patient who has a catecholamine-secreting tumor. In embodiments, a GRA is used in combination with somatostatin, or somatostatin receptor agonists (e.g., somatostatin analogs) to control catecholamine excess, to ameliorate the symptoms of catecholamine excess, to treat Cushing's syndrome, or all three, in a patient who has a catecholamine-secreting tumor. In embodiments, a GRA is used in combination with chemotherapy, somatostatin, or somatostatin receptor agonists (e.g., somatostatin analogs) to control catecholamine excess, to ameliorate the symptoms of catecholamine excess, to treat Cushing's syndrome, or all three, in a patient who has a catecholamine-secreting tumor. In embodiments, the somatostatin, or somatostatin analogs or receptor agonists are used in imaging (e.g., imaging of a tumor). In embodiments, the GRA is administered once daily. In embodiments, the GRA is administered once daily with or soon after a meal.

In embodiments, a GRA is used in combination with alpha-adrenergic and/or beta-adrenergic receptor antagonists to control catecholamine excess, to ameliorate the symptoms of catecholamine excess, to treat Cushing's syndrome, or all three, in a patient who has a catecholamine-secreting tumor. In embodiments, a GRA is used in combination with chemotherapy and alpha or beta-adrenergic receptor antagonists to control catecholamine excess, to ameliorate the symptoms of catecholamine excess, to treat Cushing's syndrome, or all three, in a patient who has a catecholamine-secreting tumor. In embodiments, a GRA is used in combination with a radiotherapy agent (e.g., a compound including a radioactive moiety, such as a peptide for use in Peptide Receptor Radionuclide Therapy (PRRT)) to control catecholamine excess, to ameliorate the symptoms of catecholamine excess, to treat Cushing's syndrome, or all three, in a patient who has a catecholamine-secreting tumor. In embodiments, a GRA is used in combination with chemotherapy and a radiotherapy agent (e.g., a compound including a radioactive moiety, such as a peptide for use in Peptide Receptor Radionuclide Therapy (PRRT)) to control catecholamine excess, to ameliorate the symptoms of catecholamine excess, to treat Cushing's syndrome, or all three, in a patient who has a catecholamine-secreting tumor. In embodiments, the GRA is administered once daily. In embodiments, the GRA is administered once daily with or soon after a meal.

In some cases, the patient is administered a composition consisting essentially of a glucocorticoid receptor antagonist (GRA) in an amount effective to reduce the catecholamine secretion in a patient who has a catecholamine-secreting tumor. In embodiments, the patient is a Cushing's syndrome patient, and is administered a composition consisting essentially of a GRA in an amount effective to treat Cushing's syndrome and to reduce the catecholamine secretion in a patient who has a catecholamine-secreting tumor. In some cases, the patient is administered a composition consisting essentially of a GRA in an amount effective to ameliorate the symptoms of catecholamine excess in a patient who has a catecholamine-secreting tumor. In embodiments, the patient is administered a composition comprising a GRA in an amount effective to reduce the catecholamine production or catecholamine secretion in a patient who has a catecholamine-secreting tumor, and is administered another agent; the other agent may be administered in combination with, or administered concurrently with, or may be administered at different times than, the GRA. In embodiments, the patient is administered a composition comprising a GRA in an amount effective to ameliorate the symptoms of catecholamine excess in a patient who has a catecholamine-secreting tumor, and is administered another agent; the other agent may be administered in combination with, or administered concurrently with, or may be administered at different times than, the GRA. In embodiments, the patient is administered a composition comprising a GRA in an amount effective to treat Cushing's syndrome. In embodiments, the patient is administered a composition comprising a GRA in an amount effective to treat Cushing's syndrome and to provide one or more of the other benefits disclosed herein.

In embodiments, the other agent may be a chemotherapy agent; or an adrenergic blocker (e.g., may be an alpha-adrenergic receptor blocker, or a beta-adrenergic receptor blocker, or an adrenergic antagonist active at both an alpha- and a beta-adrenergic receptor); or somatostatin or a somatostatin analog; or a radiotherapy agent (e.g., a compound including a radioactive moiety, such as a peptide for use in Peptide Receptor Radionuclide Therapy (PRRT)); and combinations thereof. In embodiments, methods disclosed herein comprising treating a patient with a GRA and another agent include, for example, methods for treating a patient receiving chemotherapy for the treatment of a catecholamine-secreting neuroendocrine tumor; methods for treating a Cushing's syndrome patient receiving chemotherapy for the treatment of a catecholamine-secreting neuroendocrine tumor; methods for treating a patient receiving an alpha-adrenergic receptor blocker, or a beta-adrenergic receptor blocker, or both, for the treatment of a catecholamine-secreting neuroendocrine tumor in the patient; methods for treating a patient receiving an alpha-adrenergic receptor blocker, or a beta-adrenergic receptor blocker, or both, for the treatment of a catecholamine-secreting neuroendocrine tumor; methods for treating a patient receiving a somatostatin analog for treatment of a catecholamine-secreting neuroendocrine tumor; methods for treating a patient receiving a somatostatin analog for imaging related to diagnosis or treatment of a catecholamine-secreting neuroendocrine tumor; and methods for treating a patient receiving Peptide Receptor Radionuclide Therapy (PRRT) for the treatment of a catecholamine-secreting neuroendocrine tumor. In embodiments, the GRA is administered once daily. In embodiments, the GRA is administered once daily with or soon after a meal.

In embodiments of the methods of treating a patient who has a catecholamine-secreting tumor, the patient is administered a composition comprising another active agent and a GRA in an amount effective to reduce the catecholamine secretion in a patient who has a catecholamine-secreting tumor. In embodiments the patient who has a catecholamine-secreting tumor is a Cushing's syndrome patient, and the patient is administered a composition comprising another active agent and a GRA in an amount effective to treat Cushing's syndrome and to reduce the catecholamine secretion in a patient who has a catecholamine-secreting tumor. In embodiments, the patient is administered a composition comprising another active agent and a GRA in an amount effective to ameliorate the symptoms of catecholamine excess in a patient who has a catecholamine-secreting tumor. In embodiments, the other agent may be an adrenergic blocker (e.g., may be an alpha-adrenergic receptor blocker, or a beta-adrenergic receptor blocker, or an adrenergic antagonist active at both an alpha- and a beta-adrenergic receptor); may be somatostatin; and may be a somatostatin analog. In embodiments, composition may comprise a GRA and a combination of two or more of the other agents, where the other agents are selected from adrenergic blockers (e.g., alpha-adrenergic receptor blockers and beta-adrenergic receptor blockers, somatostatin, and somatostatin analogs. In embodiments, the GRA is administered once daily. In embodiments, the GRA is administered once daily with or soon after a meal.

In embodiments, the methods disclosed herein include methods of reducing the catecholamine production and tumor burden in a patient who has a metastatic or unresectable catecholamine-secreting tumor, the method comprising administering an effective amount of mifepristone at a daily dose of between 0.1 and 50 mg/kg/day for at least 5 weeks. In embodiments, the patient is a Cushing's syndrome patient, and the treatment is effective to treat Cushing's syndrome in the patient. In embodiments, the methods disclosed herein include methods of reducing the catecholamine production and tumor burden in a patient, such as a Cushing's syndrome patient, who has a metastatic or unresectable catecholamine-secreting tumor, the method comprising administering an effective amount of mifepristone at a daily dose of between 0.1 and 50 mg/kg/day for at least 5 weeks with the proviso that the patient is not simultaneously being administered an exogenous glucocorticoid receptor agonist. In embodiments, the methods disclosed herein include methods of reducing the catecholamine production and tumor burden in a patient, such as a Cushing's syndrome patient, who has a metastatic or unresectable catecholamine-secreting tumor, the method comprising administering an effective amount of mifepristone at a daily dose of between 0.1 and 50 mg/kg/day for at least 5 weeks with the proviso that: i) the patient is not otherwise in need of treatment with a glucocorticoid receptor antagonist, and ii) the patient is not simultaneously being administered an exogenous glucocorticoid receptor agonist. In embodiments, these methods comprise administering an effective amount of mifepristone at a daily dose of between 0.1 and 100 mg/kg/day, or of between 0.1 and 20 mg/kg/day, or of between 0.1 and 15 mg/kg/day, or of between 0.1 and 12 mg/kg/day, or of between 0.1 and 10 mg/kg/day, or of between 0.1 and 5 mg/kg/day, or of between 0.1 and 3 mg/kg/day, or of between 0.1 and 1 mg/kg/day, for at least 5 weeks with the same proviso. In embodiments, the GRA is administered once daily. In embodiments, the GRA is administered once daily with or soon after a meal.

In some cases, the patient is administered a composition consisting essentially of mifepristone in an amount effective to reduce the catecholamine secretion in a patient who has a catecholamine-secreting tumor. In embodiments, the patient is a Cushing's syndrome patient. In some cases, the patient is administered a composition consisting essentially of mifepristone in an amount effective to ameliorate the symptoms of catecholamine excess in a patient who has a catecholamine-secreting tumor. In embodiments of the methods disclosed herein, the patient is administered a composition comprising another active agent and comprising mifepristone in an amount effective to reduce the catecholamine secretion in a patient who has a catecholamine-secreting tumor. In embodiments of the methods disclosed herein, the patient is administered a composition comprising another active agent and comprising mifepristone in an amount effective to ameliorate the symptoms of catecholamine excess in a patient who has a catecholamine-secreting tumor. In embodiments, the other active agent is an adrenergic blocker (e.g., may be an alpha-adrenergic receptor blocker, or a beta-adrenergic receptor blocker, or an adrenergic antagonist active at both an alpha- and a beta-adrenergic receptor); or somatostatin; or a somatostatin analog; or may include combinations thereof. In embodiments, the GRA is administered once daily. In embodiments, the GRA is administered once daily with or soon after a meal.

In some cases, the catecholamine-secreting tumor is a pheochromocytoma. In some cases, the catecholamine-secreting tumor is a paraganglioma. In some cases, the patient suffers from metastatic catecholamine-secreting tumors. In some embodiments, the patient has an unresectable not malignant tumor. In some embodiments, the patient has an unresectable, multifocal non-malignant tumor. In embodiments, the patient is a Cushing's syndrome patient with a tumor, wherein the tumor is a pheochromocytoma, or is a paraganglioma, or is a metastatic catecholamine-secreting tumor, or is an unresectable not malignant tumor, or is an unresectable multifocal non malignant tumor. In embodiments, the GRM, such as a GRA, is administered once daily. In embodiments, the GRM, such as a GRA, is administered once daily with or soon after a meal.

Compositions

Applicant discloses herein compositions comprising a glucocorticoid receptor antagonist (GRA) which may be used in the treatment of a patient having a catecholamine-secreting tumor. In embodiments, the compositions comprising a GRA may be provided in an amount effective to reduce the catecholamine secretion in a patient who has a catecholamine-secreting tumor, or in an amount effective to ameliorate the symptoms of catecholamine excess in a patient who has a catecholamine-secreting tumor, or both.

Applicant also discloses herein compositions comprising a glucocorticoid receptor antagonist (GRA) and another active agent, where the other active agent may be an adrenergic blocker (e.g., may be an alpha-adrenergic receptor blocker, or a beta-adrenergic receptor blocker, or an adrenergic antagonist active at both an alpha- and a beta-adrenergic receptor); or somatostatin; or a somatostatin analog; or may include combinations thereof. These compositions comprising a GRA and another active agent may be used in the treatment of a patient having a catecholamine-secreting tumor. In embodiments, the compositions comprising a GRA and another active agent may include amounts of GRA, another active agent, or both, effective to reduce the catecholamine secretion in a patient who has a catecholamine-secreting tumor. In embodiments, the compositions comprising a GRA and another active agent may include amounts of GRA, another active agent, or both, in amounts effective to ameliorate the symptoms of catecholamine excess in a patient who has a catecholamine-secreting tumor.

The compositions as disclosed herein can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions disclosed herein can be administered by inhalation, for example, intranasally. Additionally, the compositions of the present invention can be administered transdermally. The compositions disclosed herein can also be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

Accordingly, in embodiments disclosed herein, the compositions include pharmaceutical compositions including a pharmaceutically acceptable carrier or excipient, a glucocorticoid receptor antagonist (GRA), and an adrenergic antagonist. The adrenergic antagonist may be an alpha-adrenergic antagonist, may be a beta-adrenergic antagonist, and may be an adrenergic antagonist with antagonistic activity at both alpha-adrenergic receptors and beta-adrenergic receptors. In further embodiments disclosed herein, the compositions include pharmaceutical compositions including a pharmaceutically acceptable carrier or excipient, a glucocorticoid receptor antagonist (GRA), and somatostatin. In other embodiments disclosed herein, the compositions include pharmaceutical compositions including a pharmaceutically acceptable carrier or excipient, a glucocorticoid receptor antagonist (GRA), and somatostatin analog.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the other active agent and/or the GRA.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the other active agent and/or the GRA mixed with a filler or binders such as lactose or starches, lubricants such as talc or magnesium stearate, and, optionally, stabilizers. In soft capsules, the other active agent and/or the GRA may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the other active agent and/or the GRA are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the other active agent and/or the GRA in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the other active agent and/or the GRA in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

Administration

In embodiments, the compositions are administered once daily. In embodiments, the compositions are administered once daily with or soon after a meal.

The compositions disclosed herein can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the GRA and another active agent, where the other active agent is selected from an adrenergic antagonist, somatostatin, and a somatostatin analog. In embodiments, the adrenergic antagonist may be an alpha-adrenergic antagonist, a beta-adrenergic antagonist, and may be an adrenergic antagonist with activity at both alpha- and beta-adrenergic receptors. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The GRA and the other active agent can be co-administered or administered separately. Co-administration includes administering the other active agent within 0.5, 1, 2, 4, 6, 8, 10, 12, 16, 20, or 24 hours of the GRA. Co-administration also includes administering the GRA and the other active agent simultaneously, approximately simultaneously (e.g., within about 1, 5, 10, 15, 20, or 30 minutes of each other), or sequentially in any order. Moreover, the GRA and the other active agent can each be administered once a day, or two, three, or more times per day so as to provide the preferred dosage level per day.

In some embodiments, co-administration can be accomplished by co-formulation, i.e., preparing a single pharmaceutical composition including both the GRA and the other active agent. Suitable co-formulations include single pharmaceutical compositions including a GRA, another active agent, and a pharmaceutically acceptable excipient. For example, suitable co-formulations include single pharmaceutical compositions including a GRA, a pharmaceutically acceptable excipient, and an active agent selected from an adrenergic receptor antagonist (e.g., an alpha-adrenergic antagonist, a beta-adrenergic antagonist, or an adrenergic antagonist active at both alpha- and beta-adrenergic receptors), somatostatin, and a somatostatin analog.

In other embodiments, the GRA and the other active agent can be formulated separately.

The other active agent can be present in any suitable amount, and can depend on various factors including, but not limited to, weight and age of the subject, state of the disease, etc. Suitable dosage ranges for the other active agent in combination with the GRA, include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the other active agent in combination with the GRA, include about 0.1 mg, 1 mg, 5, 10, 20, 30, 40, 50, 60, 70, 80, 90, 100, 200, 300, 400, 500, 600, 700, 800, 900 or 1000 mg.

Similarly, the GRA can be present in combination with the other active agent in any suitable amount. The amount of GRA can depend on various factors including, but not limited to, weight and age of the subject, state of the disease, etc. Suitable dosage ranges for the GRA in combination with the other active agent, include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the GRA in combination with the other active agent, include, but are not limited to, about 1 mg, 5, 10, 20, 30, 40, 50, 60, 70, 80, 90, 100, 200, 300, 400, 500, 600, 700, 800, 900 or about 1000 mg.

The other active agent and the GRA can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The other active agent and the GRA can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the other active agent and the GRA are suitable in the compositions and methods disclosed herein.

The composition can also contain other compatible therapeutic agents. The compounds described herein can be used in combination with one another, or with adjunctive agents that may not be effective alone, but may contribute to the efficacy of the active agent.

Exemplary Embodiments

Embodiments of the methods and compositions disclosed herein include, without limitation, the following exemplary embodiments. Patients to be treated according to these embodiments include, without limitation, Cushing's syndrome patients with a tumor as described in the following embodiments.

A method of reducing catecholamine excess in a patient with a catecholamine-secreting tumor, the method comprising: administering an effective amount of a glucocorticoid receptor modulator to said patient, wherein said patient is i) not otherwise in need of treatment with a glucocorticoid receptor antagonist, and ii) not simultaneously being administered an exogenous glucocorticoid receptor agonist. The glucocorticoid receptor modulator (GRM) may be a glucocorticoid receptor antagonist (GRA). In methods of reducing catecholamine excess in a patient with a catecholamine-secreting tumor as disclosed herein, the GRM may be administered once per day. In embodiments of the methods of reducing catecholamine excess in a patient with a catecholamine-secreting tumor as disclosed herein, the GRM may be administered more than once per day.

In embodiments of methods of reducing catecholamine excess in a patient with a catecholamine-secreting tumor, the method comprises: administering an effective amount of mifepristone at a daily dose of between 0.1 and 100 mg/kg/day for at least 5 weeks, wherein said patient is not otherwise in need of treatment with a glucocorticoid receptor antagonist, and is not simultaneously being administered an exogenous glucocorticoid receptor agonist. In embodiments, the daily dose of mifepristone is between 0.1 and 50 mg/kg/day for at least 5 weeks. In embodiments, the daily dose of mifepristone is between 1 and 10 mg/kg/day for at least 5 weeks.

A method of ameliorating the symptoms of catecholamine excess in a patient with a catecholamine-secreting tumor, the method comprising: administering an effective amount of a GRM to said patient, wherein said patient is not otherwise in need of treatment with a GRM such as a GRA, and is not simultaneously being administered an exogenous glucocorticoid receptor agonist. In embodiments of the methods of ameliorating the symptoms of catecholamine excess in a patient with a catecholamine-secreting tumor disclosed herein, the GRM may be a GRA. In embodiments, the GRM may be administered once per day; in embodiments, the GRM may be administered more than once per day.

In embodiments of methods of ameliorating the symptoms of catecholamine excess in a patient with a catecholamine-secreting tumor, the method comprises: administering an effective amount of mifepristone at a daily dose of between 0.1 and 100 mg/kg/day for at least 5 weeks, wherein said patient is not otherwise in need of treatment with a glucocorticoid receptor antagonist, and is not simultaneously being administered an exogenous glucocorticoid receptor agonist.

In embodiments of the methods of ameliorating the symptoms of catecholamine excess in a patient with a catecholamine-secreting tumor, the daily dose of mifepristone is a once-daily dose. In further embodiments of the methods of ameliorating the symptoms of catecholamine excess in a patient with a catecholamine-secreting tumor, mifepristone is administered more than once per day. In embodiments of the methods of ameliorating the symptoms of catecholamine excess in a patient with a catecholamine-secreting tumor, the daily dose of mifepristone is between 0.1 and 20 mg/kg/day for at least 5 weeks. In embodiments of the methods of ameliorating the symptoms of catecholamine excess in a patient with a catecholamine-secreting tumor, the daily dose of mifepristone is between 0.1 and 10 mg/kg/day for at least 5 weeks.

A method to improve the efficacy of chemotherapy in patients with a catecholamine-secreting tumor, the method comprising: administering an effective amount of a glucocorticoid receptor modulator to a patient receiving chemotherapy for the treatment of a catecholamine-secreting neuroendocrine tumor in the patient, wherein said patient is not otherwise in need of treatment with a glucocorticoid receptor antagonist, and is not simultaneously being administered an exogenous glucocorticoid receptor agonist. In embodiments of the methods to improve the efficacy of chemotherapy in patients with a catecholamine-secreting tumor disclosed herein, the GRM may be a GRA.

A method to improve the efficacy of chemotherapy in patients with a catecholamine-secreting tumor, the method comprising: administering an effective amount of mifepristone at a daily dose of between 0.1 and 100 mg/kg/day for at least 5 weeks to a patient receiving chemotherapy for the treatment of a catecholamine-secreting neuroendocrine tumor in the patient, wherein said patient is not otherwise in need of treatment with a glucocorticoid receptor antagonist, and is not simultaneously being administered an exogenous glucocorticoid receptor agonist. In further embodiments of the methods to improve the efficacy of chemotherapy in patients with a catecholamine-secreting tumor, mifepristone is administered more than once per day. In embodiments of the methods to improve the efficacy of chemotherapy in patients with a catecholamine-secreting tumor, the daily dose of mifepristone is between 0.1 and 20 mg/kg/day for at least 5 weeks. In embodiments of the methods to improve the efficacy of chemotherapy in patients with a catecholamine-secreting tumor, the daily dose of mifepristone is between 0.1 and 10 mg/kg/day for at least 5 weeks.

A method to improve the efficacy of alpha and beta-adrenergic receptor blockade in a patient with a catecholamine-secreting tumor, the method comprising: administering an effective amount of a GRM to a patient receiving an alpha-adrenergic receptor blocker, or a beta-adrenergic receptor blocker, or both, for the treatment of a catecholamine-secreting neuroendocrine tumor in the patient, wherein said patient is not otherwise in need of treatment with a GRM, such as a GRA, and is not simultaneously being administered an exogenous glucocorticoid receptor agonist. In embodiments of the methods to improve the efficacy of alpha and beta-adrenergic receptor blockade in a patient with a catecholamine-secreting tumor, the GRM is a GRA.

A method to improve the efficacy of alpha and beta-adrenergic receptor blockade in a patient with a catecholamine-secreting tumor, the method comprising: administering an effective amount of mifepristone at a daily dose of between 0.1 and 100 mg/kg/day for at least 5 weeks to a patient receiving an alpha-adrenergic receptor blocker, or a beta-adrenergic receptor blocker, or both, for the treatment of a catecholamine-secreting neuroendocrine tumor in the patient, wherein said patient is not otherwise in need of treatment with a glucocorticoid receptor antagonist, and is not simultaneously being administered an exogenous glucocorticoid receptor agonist.

A method to improve the efficacy of somatostatin and somatostatin analog treatments in patients with catecholamine-secreting neuroendocrine tumors, the method comprising: administering an effective amount of a glucocorticoid receptor modulator to said patient, wherein somatostatin or a somatostatin analog is administered to the patient for treatment of a catecholamine-secreting neuroendocrine tumor in the patient, wherein said patient is not otherwise in need of treatment with a glucocorticoid receptor antagonist, and is not simultaneously being administered an exogenous glucocorticoid receptor agonist. In embodiments of the methods to improve the efficacy of somatostatin and somatostatin analog treatments in patients with a catecholamine-secreting tumor disclosed herein, the GRM may be a GRA.

A method to improve the efficacy of somatostatin and somatostatin analog treatments in patients with catecholamine-secreting neuroendocrine tumors, the method comprising: administering an effective amount of a glucocorticoid receptor modulator to said patient, wherein somatostatin or a somatostatin analog is administered to the patient for treatment of a catecholamine-secreting neuroendocrine tumor in the patient, administering an effective amount of mifepristone at a daily dose of between 0.1 and 100 mg/kg/day for at least 5 weeks to a patient receiving somatostatin or a somatostatin analog for treatment of a catecholamine-secreting neuroendocrine tumor, wherein said patient is not otherwise in need of treatment with a glucocorticoid receptor antagonist, and is not simultaneously being administered an exogenous glucocorticoid receptor agonist.

A method to improve the efficacy of somatostatin analog imaging modalities in patients with catecholamine-secreting neuroendocrine tumors, the method comprising: administering an effective amount of a glucocorticoid receptor modulator to a patient receiving a somatostatin analog for imaging related to diagnosis or treatment of a catecholamine-secreting neuroendocrine tumor, wherein said patient is not otherwise in need of treatment with a glucocorticoid receptor antagonist, and is not simultaneously being administered an exogenous glucocorticoid receptor agonist. In embodiments of the methods to improve the efficacy of somatostatin analog imaging modalities in patients with catecholamine-secreting neuroendocrine tumors, the GRM may be a GRA.

A method to improve the efficacy of somatostatin analog imaging modalities in a patient with a catecholamine-secreting tumor, the method comprising: administering an effective amount of mifepristone at a daily dose of between 0.1 and 100 mg/kg/day for at least 5 weeks to a patient receiving a somatostatin analog for imaging related to diagnosis or treatment of a catecholamine-secreting neuroendocrine tumor, wherein said patient is not otherwise in need of treatment with a glucocorticoid receptor antagonist, and is not simultaneously being administered an exogenous glucocorticoid receptor agonist.

A method to improve the efficacy of somatostatin analog imaging modalities in a patient with a catecholamine-secreting tumor, the method comprising: administering an effective amount of mifepristone at a daily dose of between 0.1 and 100 mg/kg/day for at least 5 weeks to a patient receiving a somatostatin analog for imaging related to diagnosis or treatment of a catecholamine-secreting neuroendocrine tumor, wherein said patient is not otherwise in need of treatment with a glucocorticoid receptor antagonist, and is not simultaneously being administered an exogenous glucocorticoid receptor agonist.

A method to improve the efficacy of Peptide Receptor Radionuclide Therapy (PRRT) in patients with catecholamine-secreting neuroendocrine tumors, the method comprising: administering an effective amount of a glucocorticoid receptor modulator to a patient receiving Peptide Receptor Radionuclide Therapy (PRRT) for the treatment of a catecholamine-secreting neuroendocrine tumor, wherein said patient is not otherwise in need of treatment with a glucocorticoid receptor antagonist, and is not simultaneously being administered an exogenous glucocorticoid receptor agonist.

A method to improve the efficacy of Peptide Receptor Radionuclide Therapy (PRRT) in a patient with a catecholamine-secreting tumor, the method comprising: administering an effective amount of mifepristone at a daily dose of between 0.1 and 100 mg/kg/day for at least 5 weeks to a patient receiving Peptide Receptor Radionuclide Therapy (PRRT) for treatment of a catecholamine-secreting neuroendocrine tumor, wherein said patient is not otherwise in need of treatment with a glucocorticoid receptor antagonist, and is not simultaneously being administered an exogenous glucocorticoid receptor agonist.

In any or all of the methods disclosed herein, including, e.g., methods of reducing catecholamine excess in a patient with a catecholamine-secreting tumor; methods of ameliorating the symptoms of catecholamine excess in a patient with a catecholamine-secreting tumor; methods to improve the efficacy of chemotherapy in patients with a catecholamine-secreting tumor; methods to improve the efficacy of alpha and beta-adrenergic receptor blockade in a patient with a catecholamine-secreting tumor; methods to improve the efficacy of somatostatin and somatostatin analog treatments in patients with catecholamine-secreting neuroendocrine tumors; methods to improve the efficacy of somatostatin analog imaging modalities in patients with catecholamine-secreting neuroendocrine tumors; and methods to improve the efficacy of Peptide Receptor Radionuclide Therapy (PRRT) in patients with catecholamine-secreting neuroendocrine tumors, the GRM may be mifepristone. In embodiments, the GRM may be a GRA that binds with higher affinity to a type II glucocorticoid receptor (GR-II) than to a type I glucocorticoid receptor (GR-I). In embodiments, the GRM may be a GRA that binds with higher affinity to a GR-II than to a GR-I, and further binds to a progesterone receptor (PR). In embodiments, the GRM is a GRA that binds to a GR-II with a binding constant of less than about 10 nanomolar (nM). In embodiments, the GRM is a GRA that binds to a GR-II with a binding constant of less than about 5 nM. In embodiments, the GRM is a GRA that binds to a GR-II with a binding constant of less than about 2 nM. In embodiments, the GRM is a GRA that binds to a GR-II with a binding constant of less than about 1 nM. In embodiments, the GRM is a GRA that binds to a GR-II with a binding constant of less than about 10 nanomolar (nM), and further binds to a PR with a binding constant of less than about 10 nM. In embodiments, the GRM is a GRA that binds to a GR-II with a binding constant of less than about 10 nanomolar (nM), and further binds to a PR with a binding constant of more than about 500 nM. In embodiments, the GRM is a GRA that binds to a GR-II with a binding constant of less than about 10 nanomolar (nM), and further binds to a PR with a binding constant of more than about 1000 nM. In embodiments in which the GRM binds to a PR with a binding constant of more than about 500 nM or more than about 1000 nM, the GRM may be a GRA that binds to a GR-II with a binding constant of less than about 5 nM, or less than about 2 nM, or less than about 1 nM.

In any or all of the methods disclosed herein, including, e.g., methods of reducing catecholamine excess in a patient with a catecholamine-secreting tumor; methods of ameliorating the symptoms of catecholamine excess in a patient with a catecholamine-secreting tumor; methods to improve the efficacy of chemotherapy in patients with a catecholamine-secreting tumor; methods to improve the efficacy of alpha and beta-adrenergic receptor blockade in a patient with a catecholamine-secreting tumor; methods to improve the efficacy of somatostatin and somatostatin analog treatments in patients with catecholamine-secreting neuroendocrine tumors; methods to improve the efficacy of somatostatin analog imaging modalities in patients with catecholamine-secreting neuroendocrine tumors; and methods to improve the efficacy of Peptide Receptor Radionuclide Therapy (PRRT) in patients with catecholamine-secreting neuroendocrine tumors, the GRM may be administered once per day. In further embodiments, the GRM may be administered more than once per day. In embodiments, the GRM may be administered at a daily dose of between 1 and 1000 mg/kg/day. In embodiments, the GRM may be administered daily for at least 5 weeks. In embodiments, the GRM may be administered at a daily dose of between 1 and 100 mg/kg/day. In embodiments, the GRM may be administered at a daily dose of between 1 and 100 mg/kg/day for at least 5 weeks. In embodiments, the GRM may be administered at a daily dose of between 1 and 50 mg/kg/day. In embodiments, the GRM may be administered at a daily dose of between 1 and 50 mg/kg/day for at least 5 weeks. In embodiments, the GRM may be administered at a daily dose of between 1 and 20 mg/kg/day. In embodiments, the GRM may be administered at a daily dose of between 1 and 20 mg/kg/day for at least 5 weeks.

In embodiments, the methods comprise administering an effective amount of mifepristone at a daily dose of between 0.1 and 100 mg/kg/day for at least 5 weeks, wherein said patient is not otherwise in need of treatment with a glucocorticoid receptor antagonist, and is not simultaneously being administered an exogenous glucocorticoid receptor agonist. In embodiments, the daily dose of mifepristone is between 0.1 and 50 mg/kg/day for at least 5 weeks. In embodiments, the daily dose of mifepristone is between 1 and 10 mg/kg/day for at least 5 weeks.

In further embodiments, Applicant discloses pharmaceutical compositions herein.

For example, Applicant discloses a pharmaceutical composition comprising a glucocorticoid receptor antagonist in an amount effective for the treatment of a patient having a catecholamine-secreting tumor; a pharmaceutical composition comprising a glucocorticoid receptor antagonist in an amount effective to reduce the effects of catecholamine excess in a patient having a catecholamine-secreting tumor. In embodiments of the pharmaceutical compositions, the treatment of the patient with the composition is effective to reduce the catecholamine production in the tumor of the patient, to reduce the effects of catecholamine excess in the patient, or both. In embodiments of the pharmaceutical compositions, the GRA is selected from a steroidal glucocorticoid receptor antagonist, a GRA having a cyclohexyl-pyrimidine backbone; a GRA having a fused azadecalin backbone; a GRA having a heteroaryl ketone fused azadecalin backbone; or a GRA having an octahydro fused azadecalin backbone. In embodiments of the pharmaceutical compositions, the GRA is mifepristone.

Applicant also discloses pharmaceutical composition comprising a glucocorticoid receptor antagonist (GRA) and another active agent, wherein the GRA and the other agent are present in amounts effective to reduce the catecholamine production in the tumor of the patient, to reduce the effects of catecholamine excess in the patient, or both. In embodiments, the GRA is selected from a steroidal glucocorticoid receptor antagonist, a GRA having a cyclohexyl-pyrimidine backbone; a GRA having a fused azadecalin backbone; a GRA having a heteroaryl ketone fused azadecalin backbone; or a GRA having an octahydro fused azadecalin backbone. In embodiments, the GRA is mifepristone.

In embodiments, the other agent is an adrenergic antagonist. In embodiments, the other agent is an adrenergic antagonist selected from an alpha-adrenergic receptor blocker, or a beta-adrenergic receptor blocker, or an adrenergic antagonist active at both an alpha- and a beta-adrenergic receptor. In embodiments, the other agent comprises an adrenergic antagonist in an amount effective to reduce the catecholamine production in the tumor of the patient, to reduce the effects of catecholamine excess in the patient, or both.

In embodiments, the other agent is somatostatin or a somatostatin analog. In embodiments, the composition comprises somatostatin or a somatostatin analog in an amount effective to reduce the catecholamine production in the tumor of the patient, to reduce the effects of catecholamine excess in the patient, or both.

EXAMPLES

The following examples are presented by way of illustration of embodiments of the methods disclosed herein, and serve to illustrate, but not to limit, the present disclosure of methods of treating patients with catecholamine-secreting tumors.

Example 1

A 53 year-old female with metastatic pheochromocytoma associated with ectopic ACTH secretion unresponsive to conventional chemotherapy with CVD (cyclophosphamide, vincristine and dacarbazine) and Sunitinib (tyrosine kinase inhibitors) was enrolled in a phase 2 study with a somatostatin analog. After 3 months of therapy her metanephrine levels remained significantly elevated and she continued to experience significant catecholamine excess symptoms (palpitations, tremors and panic attacks) despite the use of a high dose of atenolol (beta blocker) and phenoxybenzamine (alpha blocker). At the same time the diagnosis of Cushing syndrome was made and 300 mg of Mifepristone was added to her regimen and the dose was further increased to 600 mg daily two weeks later. One week after the institution of mifepristone she noted a dramatic improvement in her symptoms related to cortisol excess as well as to catecholamine excess. The plasma epinephrine level after 2 weeks of therapy with mifepristone was decreased by 50%, and the plasma metanephrine level was decreased by 25% after 9 weeks of therapy. After 3 months of therapy with mifepristone her symptoms of catecholamine excess were controlled, the metanephrine level was slightly elevated but she developed vaginal bleeding and mifepristone was temporarily withheld. One week after the discontinuation of mifepristone she experienced worse symptoms of catecholamine excess. Metanephrine measurement showed a fourfold increase compared to the level of metanephrine measurements obtained during mifepristone dosing.

Example 2

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 50 mg/kg/day. A measurement indicates that the blood level of a catecholamine is lower after five weeks of treatment as compared to the initial level.

Example 3

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 20 mg/kg/day. A measurement indicates that the blood level of a catecholamine is lower after five weeks of treatment as compared to the initial level.

Example 4

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 15 mg/kg/day. A measurement indicates that the blood level of a catecholamine is lower after five weeks of treatment as compared to the initial level.

Example 5

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 10 mg/kg/day. A measurement indicates that the blood level of a catecholamine is lower after five weeks of treatment as compared to the initial level.

Example 6

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 5 mg/kg/day. A measurement indicates that the blood level of a catecholamine is lower after five weeks of treatment as compared to the initial level.

Example 7

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 50 mg/kg/day, and is also administered chemotherapy. A measurement indicates that the blood level of a catecholamine is lower after five weeks of treatment as compared to the initial level.

Example 8

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 20 mg/kg/day, and is also administered chemotherapy. A measurement indicates that the blood level of a catecholamine is lower after five weeks of treatment as compared to the initial level.

Example 9

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 15 mg/kg/day, and is also administered chemotherapy. A measurement indicates that the blood level of a catecholamine is lower after five weeks of treatment as compared to the initial level.

Example 10

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 10 mg/kg/day, and is also administered chemotherapy. A measurement indicates that the blood level of a catecholamine is lower after five weeks of treatment as compared to the initial level.

Example 11

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 5 mg/kg/day, and is also administered chemotherapy. A measurement indicates that the blood level of a catecholamine is lower after five weeks of treatment as compared to the initial level.

Example 12

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 50 mg/kg/day, and is also administered an adrenergic antagonist. A measurement indicates that the blood level of a catecholamine is lower after five weeks of treatment as compared to the initial level.

Example 13

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 20 mg/kg/day, and is also administered an adrenergic antagonist. A measurement indicates that the blood level of a catecholamine is lower after five weeks of treatment as compared to the initial level.

Example 14

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 10 mg/kg/day, and is also administered an adrenergic antagonist. A measurement indicates that the blood level of a catecholamine is lower after five weeks of treatment as compared to the initial level.

Example 15

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 5 mg/kg/day, and is also administered an adrenergic antagonist. A measurement indicates that the blood level of a catecholamine is lower after five weeks of treatment as compared to the initial level.

Example 16

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 20 mg/kg/day, and is also administered chemotherapy and an adrenergic antagonist. A measurement indicates that the blood level of a catecholamine is lower after five weeks of treatment as compared to the initial level.

Example 17

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 20 mg/kg/day, and is also administered somatostatin. A measurement indicates that the blood level of a catecholamine is lower after five weeks of treatment as compared to the initial level.

Example 18

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 10 mg/kg/day, and is also administered somatostatin. A measurement indicates that the blood level of a catecholamine is lower after five weeks of treatment as compared to the initial level.

Example 19

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 5 mg/kg/day, and is also administered somatostatin. A measurement indicates that the blood level of a catecholamine is lower after five weeks of treatment as compared to the initial level.

Example 20

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 1 mg/kg/day, and is also administered somatostatin. A measurement indicates that the blood level of a catecholamine is lower after five weeks of treatment as compared to the initial level.

Example 21

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 20 mg/kg/day, and is also administered chemotherapy and somatostatin. A measurement indicates that the blood level of a catecholamine is lower after five weeks of treatment as compared to the initial level.

Example 22

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 20 mg/kg/day, and is also administered a somatostatin analog. A measurement indicates that the blood level of a catecholamine is lower after five weeks of treatment as compared to the initial level.

Example 23

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 15 mg/kg/day, and is also administered a somatostatin analog. A measurement indicates that the blood level of a catecholamine is lower after five weeks of treatment as compared to the initial level.

Example 24

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 10 mg/kg/day, and is also administered a somatostatin analog. A measurement indicates that the blood level of a catecholamine is lower after five weeks of treatment as compared to the initial level.

Example 25

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 5 mg/kg/day, and is also administered a somatostatin analog. A measurement indicates that the blood level of a catecholamine is lower after five weeks of treatment as compared to the initial level.

Example 26

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 20 mg/kg/day, and is also administered chemotherapy and a somatostatin analog. A measurement indicates that the blood level of a catecholamine is lower after five weeks of treatment as compared to the initial level.

Example 27

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 20 mg/kg/day, and also receives Peptide Receptor Radionuclide Therapy. A measurement indicates that the blood level of a catecholamine is lower after five weeks of treatment as compared to the initial level.

Example 28

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 15 mg/kg/day, and also receives Peptide Receptor Radionuclide Therapy. A measurement indicates that the blood level of a catecholamine is lower after five weeks of treatment as compared to the initial level.

Example 29

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 10 mg/kg/day, and also receives Peptide Receptor Radionuclide Therapy. A measurement indicates that the blood level of a catecholamine is lower after five weeks of treatment as compared to the initial level.

Example 30

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 5 mg/kg/day, and also receives Peptide Receptor Radionuclide Therapy. A measurement indicates that the blood level of a catecholamine is lower after five weeks of treatment as compared to the initial level.

Example 31

A patient having a metastatic or unresectable catecholamine-secreting tumor, who is not in need of treatment with a glucocorticoid receptor antagonist, and is not receiving exogenous glucocorticoid receptor agonist treatment, is administered an effective amount of mifepristone at a daily dose of 20 mg/kg/day, and is also administered an adrenergic antagonist, and further receives Peptide Receptor Radionuclide Therapy. A measurement indicates that the blood level of a catecholamine is lower after five weeks of treatment as compared to the initial level.

Example 32

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 100 mg/kg/day. A measurement indicates that the blood level of a catecholamine is lower after five weeks of treatment as compared to the initial level.

Example 33

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 50 mg/kg/day. A measurement indicates that the blood level of a catecholamine is lower after five weeks of treatment as compared to the initial level.

Example 34

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 20 mg/kg/day. A measurement indicates that the blood level of a catecholamine is lower after five weeks of treatment as compared to the initial level.

Example 35

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 15 mg/kg/day. A measurement indicates that the blood level of a catecholamine is lower after five weeks of treatment as compared to the initial level.

Example 36

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 10 mg/kg/day. A measurement indicates that the blood level of a catecholamine is lower after five weeks of treatment as compared to the initial level.

Example 37

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 100 mg/kg/day, and is also administered chemotherapy. A measurement indicates that the blood level of a catecholamine is lower after five weeks of treatment as compared to the initial level.

Example 38

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 50 mg/kg/day, and is also administered chemotherapy. A measurement indicates that the blood level of a catecholamine is lower after five weeks of treatment as compared to the initial level.

Example 39

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 20 mg/kg/day, and is also administered chemotherapy. A measurement indicates that the blood level of a catecholamine is lower after five weeks of treatment as compared to the initial level.

Example 40

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 15 mg/kg/day, and is also administered chemotherapy. A measurement indicates that the blood level of a catecholamine is lower after five weeks of treatment as compared to the initial level.

Example 41

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 10 mg/kg/day, and is also administered chemotherapy. A measurement indicates that the blood level of a catecholamine is lower after five weeks of treatment as compared to the initial level.

Example 42

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 50 mg/kg/day, and is also administered an adrenergic antagonist. A measurement indicates that the blood level of a catecholamine is lower after five weeks of treatment as compared to the initial level.

Example 43

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 20 mg/kg/day, and is also administered an adrenergic antagonist. A measurement indicates that the blood level of a catecholamine is lower after five weeks of treatment as compared to the initial level.

Example 44

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA)

selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 15 mg/kg/day, and is also administered an adrenergic antagonist. A measurement indicates that the blood level of a catecholamine is lower after five weeks of treatment as compared to the initial level.

Example 45

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 10 mg/kg/day, and is also administered an adrenergic antagonist. A measurement indicates that the blood level of a catecholamine is lower after five weeks of treatment as compared to the initial level.

Example 46

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 50 mg/kg/day, and is also administered chemotherapy and an adrenergic antagonist. A measurement indicates that the blood level of a catecholamine is lower after five weeks of treatment as compared to the initial level.

Example 47

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 50 mg/kg/day, and is also administered somatostatin. A measurement indicates that the blood level of a catecholamine is lower after five weeks of treatment as compared to the initial level.

Example 48

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 20 mg/kg/day, and is also administered somatostatin. A measurement indicates that the blood level of a catecholamine is lower after five weeks of treatment as compared to the initial level.

Example 49

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 15 mg/kg/day, and is also administered somatostatin. A measurement indicates that the blood level of a catecholamine is lower after five weeks of treatment as compared to the initial level.

Example 50

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 10 mg/kg/day, and is also administered somatostatin. A measurement indicates that the blood level of a catecholamine is lower after five weeks of treatment as compared to the initial level.

Example 51

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 50 mg/kg/day, and is also administered chemotherapy and somatostatin. A measurement indicates that the blood level of a catecholamine is lower after five weeks of treatment as compared to the initial level.

Example 52

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 50 mg/kg/day, and is also administered a somatostatin analog. A measurement indicates that the blood level of a catecholamine is lower after five weeks of treatment as compared to the initial level.

Example 53

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 20 mg/kg/day, and is also administered a somatostatin analog. A measurement indicates that the blood level of a catecholamine is lower after five weeks of treatment as compared to the initial level.

Example 54

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 15 mg/kg/day, and is also administered a somatostatin analog. A measurement indicates that the blood level of a catecholamine is lower after five weeks of treatment as compared to the initial level.

Example 55

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 10 mg/kg/day, and is also administered a somatostatin analog. A measurement indicates that the blood level of a catecholamine is lower after five weeks of treatment as compared to the initial level.

Example 56

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 20 mg/kg/day, and is also administered chemotherapy and a somatostatin analog. A measurement indicates that the blood level of a catecholamine is lower after five weeks of treatment as compared to the initial level.

Example 57

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 50 mg/kg/day, and also receives Peptide Receptor Radionuclide Therapy. A measurement indicates that the blood level of a catecholamine is lower after five weeks of treatment as compared to the initial level.

Example 58

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 20 mg/kg/day, and also receives Peptide Receptor Radionuclide Therapy. A measurement indicates that the blood level of a catecholamine is lower after five weeks of treatment as compared to the initial level.

Example 59

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 15 mg/kg/day, and also receives Peptide Receptor Radionuclide Therapy. A measurement indicates that the blood level of a catecholamine is lower after five weeks of treatment as compared to the initial level.

Example 60

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 10 mg/kg/day, and also receives Peptide Receptor Radionuclide Therapy. A measurement indicates that the blood level of a catecholamine is lower after five weeks of treatment as compared to the initial level.

Example 61

A patient having a metastatic or unresectable catecholamine-secreting tumor, who is not in need of treatment with a glucocorticoid receptor antagonist, and is not receiving exogenous glucocorticoid receptor agonist treatment, is administered a glucocorticoid receptor antagonist (GRA) selected from a GRA having a cyclohexyl-pyrimidine backbone; a GRA having a fused azadecalin backbone; a GRA having a heteroaryl ketone fused azadecalin backbone; and a GRA having an octahydro fused azadecalin backbone at a daily dose of 50 mg/kg/day, and is also administered an adrenergic antagonist, and further receives Peptide Receptor Radionuclide Therapy. A measurement indicates that the blood level of a catecholamine is lower after five weeks of treatment as compared to the initial level.

Example 62

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 300 mg mifepristone and an adrenergic antagonist on a daily basis for five weeks. A measurement indicates that the blood level of a catecholamine is lower after five weeks of treatment as compared to the initial level.

Example 63

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 100 mg mifepristone and an adrenergic antagonist on a daily basis for five weeks. A measurement indicates that the blood level of a catecholamine is lower after five weeks of treatment as compared to the initial level.

Example 64

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 300 mg mifepristone and an adrenergic antagonist on a daily basis for five weeks. A measurement indicates that the blood level of a catecholamine is lower after five weeks of treatment as compared to the initial level.

Example 65

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 300 mg mifepristone and an adrenergic antagonist on a daily basis for five weeks. A measurement indicates that the blood level of a catecholamine is lower after five weeks of treatment as compared to the initial level.

Example 66

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 100 mg mifepristone and an adrenergic antagonist on a daily basis for five weeks. A measurement indicates that the blood level of a catecholamine is lower after five weeks of treatment as compared to the initial level.

Example 67

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 300 mg mifepristone and an adrenergic antagonist on a daily basis for five weeks, and is also administered chemotherapy. A measurement indicates that the blood level of a catecholamine is lower after five weeks of treatment as compared to the initial level.

Example 68

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 100 mg mifepristone and an adrenergic antagonist on a daily basis for five weeks, and is also administered chemotherapy. A measurement indicates that the blood level of a catecholamine is lower after five weeks of treatment as compared to the initial level.

Example 69

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 300 mg mifepristone and an adrenergic antagonist on a daily basis for five weeks, and is also administered chemotherapy. A measurement indicates that the blood level of a catecholamine is lower after five weeks of treatment as compared to the initial level.

Example 70

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 100 mg mifepristone and an adrenergic antagonist on a daily basis for five weeks, and is also administered chemotherapy. A measurement indicates that the blood level of a catecholamine is lower after five weeks of treatment as compared to the initial level.

Example 71

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 50 mg mifepristone and an adrenergic antagonist on a daily basis for five weeks, and is also administered chemotherapy. A measurement indicates that the blood level of a catecholamine is lower after five weeks of treatment as compared to the initial level.

Example 72

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 300 mg mifepristone and somatostatin on a daily basis for five weeks. A measurement indicates that the blood level of a catecholamine is lower after five weeks of treatment as compared to the initial level.

Example 73

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 100 mg mifepristone and somatostatin on a daily basis for five weeks. A measurement indicates that the blood level of a catecholamine is lower after five weeks of treatment as compared to the initial level.

Example 74

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 50 mg mifepristone and somatostatin on a daily basis for five weeks. A measurement indicates that the blood level of a catecholamine is lower after five weeks of treatment as compared to the initial level.

Example 75

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 300 mg mifepristone and a somatostatin analog on a daily basis for five weeks. A measurement indicates that the blood level of a catecholamine is lower after five weeks of treatment as compared to the initial level.

Example 76

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 100 mg mifepristone and a somatostatin analog on a daily basis for five weeks. A measurement indicates that the blood level of a catecholamine is lower after five weeks of treatment as compared to the initial level.

Example 77

A patient having a metastatic or unresectable catecholamine-secreting tumor, who is not in need of treatment with a glucocorticoid receptor antagonist, and is not receiving exogenous glucocorticoid receptor agonist treatment, is administered a single pharmaceutical composition comprising 50 mg mifepristone and a somatostatin analog on a daily basis for five weeks. A measurement indicates that the blood level of a catecholamine is lower after five weeks of treatment as compared to the initial level.

All references discussed in the present application, including all patents, patent applications, and publications cited herein, are hereby expressly incorporated by reference in their entireties.

The invention claimed is:

1. A method of reducing blood epinephrine levels and of reducing symptoms of cortisol excess in a patient with an epinephrine-secreting tumor associated with ectopic adrenocorticotropic hormone (ACTH) secretion unresponsive to conventional chemotherapy, the patient having an initial blood epinephrine level, the method comprising:
   measuring the level of ACTH and epinephrine in a sample of blood obtained from a patient with symptoms of cortisol excess and suspected of catecholamine excess to determine an initial blood epinephrine level,
   Identifying a patient with ectopic ACTH secretion, symptoms of cortisol excess and with an elevated blood epinephrine level after said patient has received conventional chemotherapy treatment, thereby determining that said patient exhibits symptoms of cortisol excess, has an epinephrine-secreting tumor associated with ectopic ACTH secretion, and that said elevated blood epinephrine level in said patient is unresponsive to conventional chemotherapy treatment, then
   Administering, to said identified patient, an amount of a glucocorticoid receptor antagonist GRA effective to reduce the blood epinephrine level of said patient by at least about 20% to about 60% as compared to said initial blood epinephrine level, and
   measuring the level of epinephrine in a further sample of blood obtained from the patient after said GRA administration to determine whether or not the measured blood epinephrine level is lower after said GRA administration than the initial blood epinephrine level,
   whereby the blood epinephrine level is reduced by at least about 20% to about 60% and symptoms of cortisol excess are reduced in said identified patient with ectopic ACTH secretion, symptoms of cortisol excess, and elevated blood epinephrine level, and with said epinephrine-secreting tumor.

2. The method of claim 1, wherein said glucocorticoid receptor antagonist binds with higher affinity to a type II glucocorticoid receptor than to a type I glucocorticoid receptor.

3. The method of claim 1, wherein said glucocorticoid receptor antagonist is administered at a daily dose of between about 1 and about 20 mg/kg/day.

4. The method of claim 1, wherein said glucocorticoid receptor antagonist is mifepristone.

5. The method of claim 1, wherein said glucocorticoid receptor antagonist is mifepristone and is administered at a daily dose of 300 milligrams (mg), 600 mg, or 900 mg per day.

6. The method of claim 5, wherein the patient is a Cushing's syndrome patient, and the method treats Cushing's syndrome in the patient.

7. The method of claim 1, wherein said glucocorticoid receptor antagonist (GRA) is administered orally at a daily dose of between about 1 and about 20 mg/kg/day.

8. The method of claim 7, wherein said glucocorticoid receptor antagonist binds with higher affinity to a type II glucocorticoid receptor than to a type I glucocorticoid receptor.

9. The method of claim 7, wherein said glucocorticoid receptor antagonist is administered daily for at least 5 weeks.

10. The method of claim 7, wherein said patient is not simultaneously being administered an exogenous glucocorticoid receptor agonist.

11. The method of claim 7, wherein said glucocorticoid receptor antagonist is mifepristone.

12. The method of claim 11, wherein said daily dose of mifepristone is 300 milligrams (mg), 600 mg, or 900 mg per day.

13. The method of claim 11, wherein the patient is a Cushing's syndrome patient, and the method treats Cushing's syndrome in the patient.

14. A method to reduce blood epinephrine levels and to improve the efficacy of chemotherapy treatment in a patient with an epinephrine-secreting neuroendocrine tumor associated with ectopic adrenocorticotropic hormone (ACTH) secretion unresponsive to conventional chemotherapy, the patient having an initial blood epinephrine level, wherein improved efficacy of chemotherapy comprises a reduced blood epinephrine level and reduced symptoms of cortisol excess, the method comprising:
   measuring the level of ACTH and epinephrine in a sample of blood obtained from a patient with symptoms of cortisol excess and suspected of epinephrine excess to determine an initial blood epinephrine level,
   Identifying a patient with ectopic ACTH secretion, symptoms of cortisol excess and with an elevated blood epinephrine level after said patient has received conventional chemotherapy treatment, thereby determining that said patient exhibits symptoms of cortisol excess, has an epinephrine-secreting tumor associated with ectopic ACTH secretion, and that said elevated blood epinephrine level in said patient is unresponsive to conventional chemotherapy treatment, then
   administering, to said identified patient, an effective amount of a glucocorticoid receptor antagonist (GRA) to a patient receiving chemotherapy for the treatment of an epinephrine-secreting neuroendocrine tumor in the patient, wherein said chemotherapy treatment does not include administration of somatostatin or of a somatostatin analog, effective to reduce the blood epinephrine level by at least about 20% to about 60% as compared to said initial blood epinephrine level in the patient receiving said chemotherapy and said GRA, and
   measuring the level of epinephrine in a further sample of blood obtained from the patient after said GRA administration to determine whether or not the measured blood epinephrine level is lower after said GRA administration than the initial blood epinephrine level,
   wherein the blood epinephrine level is reduced by at least about 20% to about 60% and symptoms of cortisol excess are reduced in said identified patient with ectopic ACTH secretion, symptoms of cortisol excess, and elevated blood epinephrine level, and with an epinephrine-secreting neuroendocrine tumor,
   whereby the blood epinephrine level is reduced and the efficacy of said chemotherapy treatment is improved.

15. The method of claim 14, wherein said glucocorticoid receptor antagonist is orally administered.

16. The method of claim 14, wherein said glucocorticoid receptor antagonist is administered at a daily dose of between about 1 and about 20 mg/kg/day.

17. The method of claim 14, wherein said glucocorticoid receptor antagonist is mifepristone.

18. The method of claim 17, wherein the mifepristone is administered at a daily dose of 300 milligrams (mg), 600 mg, or 900 mg per day.

19. The method of claim 18, wherein the patient is a Cushing's syndrome patient, and the method treats Cushing's syndrome in the patient.

20. A method to reduce the blood epinephrine level, to improve symptoms of cortisol excess, and to improve the efficacy of alpha-adrenergic and beta-adrenergic receptor blockade in a patient with an epinephrine-secreting neuroendocrine tumor associated with ectopic adrenocorticotropic hormone (ACTH) secretion unresponsive to conventional chemotherapy, the patient having an initial blood epinephrine level, the method comprising:
   measuring the level of ACTH and epinephrine in a sample of blood obtained from a patient with symptoms of cortisol excess and suspected of epinephrine excess to determine an initial blood epinephrine level,
   Identifying a patient with ectopic ACTH secretion, symptoms of cortisol excess and with an elevated blood epinephrine level after said patient has received conventional chemotherapy treatment, thereby determining that said patient exhibits symptoms of cortisol excess, has an epinephrine-secreting tumor associated with ectopic ACTH secretion, and that said elevated blood epinephrine level in said patient is unresponsive to conventional chemotherapy treatment, then
   administering, to said identified patient, a glucocorticoid receptor antagonist (GRA) at a daily dose of between 0.1 and 100 mg/kg/day for at least 5 weeks to a patient receiving an alpha-adrenergic receptor blocker, or a beta-adrenergic receptor blocker, or both, for the treatment of an epinephrine-secreting neuroendocrine tumor in the patient, wherein said GRA administration is effective to reduce the blood epinephrine level by at least about 20% to about 60% as compared to said initial blood epinephrine level in the patient having said epinephrine-secreting neuroendocrine tumor, and
   measuring the level of epinephrine in a further sample of blood obtained from the patient after said GRA administration to determine whether or not said epinephrine level is lower after said GRA administration than the initial blood epinephrine level,
   whereby the epinephrine level is reduced by at least about 20% to about 60% and symptoms of cortisol excess are reduced in said identified patient with ectopic ACTH secretion, symptoms of cortisol excess, and elevated blood epinephrine level, and with an epinephrine-secreting neuroendocrine tumor, and the efficacy of said alpha-adrenergic and beta-adrenergic receptor blockade in the patient is improved.

21. The method of claim 20, wherein said glucocorticoid receptor antagonist is orally administered.

22. The method of claim 20, wherein said glucocorticoid receptor antagonist is administered at a daily dose of between about 1 and about 20 mg/kg/day.

23. The method of claim 20, wherein said patient is not simultaneously being administered an exogenous glucocorticoid receptor agonist.

24. The method of claim 20, wherein said glucocorticoid receptor antagonist is mifepristone and is administered at a daily dose of 300 milligrams (mg), 600 mg, or 900 mg per day.

25. The method of claim 24, wherein the patient is a Cushing's syndrome patient, and the method treats Cushing's syndrome in the patient.

26. The method of claim 1 of reducing blood epinephrine level and of reducing symptoms of cortisol excess, further comprising a step to improve the efficacy of treatment with a somatostatin analog in a patient with an epinephrine-secreting neuroendocrine tumor associated with ectopic ACTH secretion, the method comprising:

further administering a somatostatin analog to said patient for treatment of said epinephrine-secreting neuroendocrine tumor in the patient, wherein said somatostatin analog administration is effective to decrease the activity of cortisol at the tumor level, whereby the blood epinephrine level and symptoms of cortisol excess are reduced and the efficacy of somatostatin analog treatment for an epinephrine-secreting neuroendocrine tumor is improved in the identified patient with the epinephrine-secreting neuroendocrine tumor.

27. The method of claim 26, wherein said glucocorticoid receptor antagonist is administered orally.

28. The method of claim 26, wherein said glucocorticoid receptor antagonist is mifepristone.

29. The method of claim 26, wherein said glucocorticoid receptor antagonist is mifepristone and is administered at a daily dose of 300 milligrams (mg), 600 mg, or 900 mg per day.

30. The method of claim 29, wherein the patient is a Cushing's syndrome patient, and the method treats Cushing's syndrome in the patient.

* * * * *

UNITED STATES PATENT AND TRADEMARK OFFICE
CERTIFICATE OF CORRECTION

PATENT NO. : 11,045,482 B2  
APPLICATION NO. : 15/915284  
DATED : June 29, 2021  
INVENTOR(S) : Andreas Moraitis Page 1 of 1

It is certified that error appears in the above-identified patent and that said Letters Patent is hereby corrected as shown below:

In the Claims

In Column 54, Line 34, Claim 1, delete "GRA" and replace with --(GRA)--

Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*